US007645580B2

(12) United States Patent
Barber et al.

(10) Patent No.: US 7,645,580 B2
(45) Date of Patent: *Jan. 12, 2010

(54) FORENSIC IDENTIFICATION

(75) Inventors: Rebecca A. L. Barber, Birmingham (GB); Michael D. Barber, Birmingham (GB); Peter E. Johnson, Birmingham (GB); Sharon M. Gillbard, Birmingham (GB); Marc D. Haywood, Birmingham (GB); Carolyn D. Smith, Birmingham (GB); Jennifer A. Arnold, Birmingham (GB); Trudy Burke, Birmingham (GB); Andrew J. Urquhart, Birmingham (GB); Peter P. Gill, Birmingham (GB)

(73) Assignee: The Secretary of State of the Home Department, Birmingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/821,259

(22) Filed: Jun. 21, 2007

(65) Prior Publication Data

US 2008/0108069 A1 May 8, 2008

Related U.S. Application Data

(63) Continuation of application No. 11/244,331, filed on Oct. 4, 2005, now abandoned, which is a continuation of application No. 09/910,183, filed on Jul. 20, 2001, now Pat. No. 7,087,380, which is a continuation of application No. 09/706,525, filed on Nov. 3, 2000, now abandoned, which is a continuation of application No. 09/498,567, filed on Feb. 4, 2000, now abandoned, which is a continuation of application No. 09/107,029, filed on Jun. 29, 1998, now abandoned.

(30) Foreign Application Priority Data

Jun. 28, 1997 (GB) .................................. 9713597.4

(51) Int. Cl.
*C12Q 1/68* (2006.01)
*C07H 21/00* (2006.01)
*C07H 21/02* (2006.01)
*C07H 21/04* (2006.01)

(52) U.S. Cl. .................... 435/6; 536/22.1; 536/23.1; 536/24.3

(58) Field of Classification Search .................. None
See application file for complete search history.

(56) References Cited

U.S. PATENT DOCUMENTS

| 5,364,759 | A | 11/1994 | Caskey et al. |
| 5,599,666 | A | 2/1997 | Schumm et al. |
| 6,156,512 | A | 12/2000 | Schumm et al. |
| RE37,984 | E | 2/2003 | Jackie et al. |
| 7,008,771 | B1 | 3/2006 | Schumm et al. |
| 7,087,380 | B2 | 8/2006 | Griffiths et al. |

OTHER PUBLICATIONS

M. D. Barber et al., *Sequence Analysis and Allelic Designation of the Two Short Tandem Repeat Loci D18S51 and D8S1179*, Int. J. Legal Med., vol. 109, 1996, pp. 62-65.
D. J. Mancuso et al., *Structure of the Gene for Human Von Willebrand Factor*, J. Biol. Chem., vol. 264, No. 33, 1989, revised Jul. 5, 2002, Database Genebank, NCBI.
Bruce Budowle et al., *Analysis of the VNTR Locus D1S80 by the PCR Followed by High-Resolution PAGE*, Am. J. Hum. Genet., vol. 48, 1991, pp. 137-144..
Al Edwards et al., *DNA Typing and Genetic Mapping with Trimeric and Tetrameric Tandem Repeats*, Am. J. Hum. Gent., vol. 49, 1991, pp. 746-756..
Colin P. Kimpton et al., *Validation of Highly Discriminating Multiplex Short Tandem Repeat Amplification Systems for Individual Identification*, Electrophoresis, vol. 17, 1996, pp. 1283-1293.
V. Sharma et al., *Tetranucleotide Repeat Polymorphism at the D21S11 Locus*, Human Moelcular Genetics, vol. 1, No. 1, 1992, p. 67.
Kevin M. Sullivan et al., *A Rapid and Quantitative DNA Set Test: Fluorescence-Based PCR Analysis of X-Y Homologous Gene Amelogenin*, BioTechniques, vol. 15, No. 4, 1993, pp. 636-641.
B. Brinkmann, *Population Genetic Comparisons Among Eight Populations Using Allele Frequency and Sequence Data From Three Microsatellite Loci*, Eur. J. Hum. Genet., vol. 4, 1996, pp. 175-182.
Cynthia J. Sprecher et al., *General Approach to Analysis of Polymorphic short Tandem Repeat Loci*, BioTechniques, vol. 20, No. 2, Feb. 1996, pp. 266-276.
B.M. Dupuy et al., *A dedicated Internal Standard in Fragment Length Analysis of Hyperpolymorphic short Tandem Repeats*, Forensic Science International, vol. 85, 1997, pp. 207-227.
Editorial, *DNA Recommendations—Further Report of the DNA Commission of the ISFH Regarding the Use of Short Tandem Systems*, Forensic Scioence International, vol. 87, 1997, pp. 179-184.
Peter Gill et al., *Report of the European DNA Profiling Group (EDNAP): An Investigation of the Complex STR Loci D21S11 and JUMFIBRA (FGA)*, Forensic Science International, vol. 86, 1997, pp. 25-33.
C. Kimpton et al., *A Further Tetranucleotide Repeat Polymorphism in the vWF Gene*, Human Molecular Genetics, vol. 1, No. 4, 1992, pp. 287.
M. Klintschar et al., *A Study of the Short Tandem Repeat Systems HUMVWA and HUMTH01 in an Austrian Population Sample*, Int. J. Legal Med., vol. 107, 1995, pp. 329-330.
Andy Urquhart et al., *Highly Discriminating Heptaplex short Tandem Repeat PCR System for Forensic Identification*, BioTechniques, vol. 18, No. 1, 1995, pp. 116-121.
Peter Gill et al., *Automated Short Tandem Repeat (STR) Analysis in Forensic Casework—A Strategy for the Future*, Electrophoresis, vol. 16, 1995, pp. 1543-1552.
Nicola J. Oldroyd et al., *A Highly Discriminating Octoplex Short Tandem Repeat Polymerase Chain Reaction System Suitable for Human Individual Identification*, Electrophoresis, vol. 16, 1995, pp. 334-337.

(Continued)

*Primary Examiner*—Ethan Whisenant
(74) *Attorney, Agent, or Firm*—Workman Nydegger

(57) ABSTRACT

The invention provides allelic ladder mixtures and individual alleles suitable for use in such mixtures. The allelic ladder mixtures give improved identification and distinguishing capabilities, particularly suitable in forensic investigations.

56 Claims, 7 Drawing Sheets

OTHER PUBLICATIONS

Kathleen A. Mills et al., *Tetranucleotide Repeat Polymorphism at the Human Alpha Fibrinogen Locus (FGA)*, Human Molecular Genetics, vol. 1, No. 9, Dec. 1992, pp. 779.

X. Tang et al., *Generation of Nineteen STS Markers that can be Anchored at Specific Sites on Human Chromosome 21*, unpublished, 1992, Genebank Accession No. M95976.

X. Tang et al., *Generation of Nineteen STS Markers that can be Anchored at Specific Sites on Human Chromosome 21*, unpublished, 1992, Genebank Accession No. M95977.

Chantal J. Fregeau et al., *DNA Typing with Fluorescently Tagged Short Tandem Repeats A Sensitive and Accurate Approach to Human Identification*, BioTechniques, vol. 15, No. 1, 1993, pp. 100-119.

S.C. Gerken et al., *Genetic and Physical Mapping of Simple Sequence Repeat Containing Sequence Tagged Sites from the Human Genome*, unpublished, 1993, Genebank Accession No. L18333.

D.W. Chung et al., *Nucleotide Sequences of the Three Genes Coding for Human Fibrinogen*, Fibrinogen, Thrombosis, Coagulation and Fibrinolysis, Plenum Press, New York, 1991, pp. 39-48, Genebank Accession No. M64982.

M. D. Barber et al., *Structural Variation in the Alleles of a Short Tandem Repeat System at the Human Alpha Fibrinogen Locus*, Int. J. Legal Med., vol. 108, 1996, pp. 180-185.

P. Gill et al., *Report of the European DNA Profiling Group (EDNAP)—Towards Standardisation of Short Tandem Repeat (STR) Loci*, Forensic Science International, vol. 65, 1994, pp. 51-59.

Colin Kimpton et al., *Evaluation of an Automated DNA Profiling System Employing Multiplex Amplification of Four Tetrameric STR Loci*, Int. J. Leg. Med., vol. 106, 1994, pp. 302-311.

A. Urquhart et al., *Variation in Short Tandem Repeat Sequences—A Survey of Twelve Microsatellite Loci for Use as Forensic Identification Markers*, Int. J. Leg. Med, vol. 107, 1994, pp. 13-20.

J. E. Lygo et al., *The Validation of Short Tandem Repeat (STR) Loci for Use in Forensic Casework*, Int. J. Leg. Med, vol. 107, 1994, pp. 77-89.

Antti Sajantila et al., *A Microsatellite Polymorphism in the von Willebrand Factor Gene: Comparison of Allele Frequencies in Different Population Samples and Evaluation for Forensic Medicine*, Forensic Science International, vol. 68, 1994, pp. 91-102.

Stig Holgersson et al., *Fluorescent-based Typing of the Two Short Tandem Repeat Loci HUMTH01 and HUMACTBP2: Reproducibility of Size Measurements and Genetic Variation in the Swedish Population*, Electrophoresis, vol. 15, 1994, pp. 890-895.

B. Brinkmann et al., *Structure of New Mutations in 2 STR Systems*, Int. J. Leg. Med, vol. 107, 1995, pp. 201-203.

P. Berschick et al., *Analysis of the Short Tandem Repeat Polymorphism D18S51: Allele Frequencies and Sequence Studies*, unpublished, 1995, Genebank Accession No. X91255.

P. Berschick et al., *Analysis of the Short Tandem Repeat Polymorphism D18S51: Allele Frequencies and Sequence Studies*, unpublished, 1995, Genebank Accession No. X91254.

P. Berschick et al., *Analysis of the Short Tandem Repeat Polymorphism D18S51: Allele Frequencies and Sequence Studies*, unpublished, 1995, Genebank Accession No. X91253.

J. Murray et al., *Cooperative Human Linkage Center*, unpublished, 1995, Genebank Accession No. G08710.

D.J. Mancuso et al., *Structure of the Gene for Human von Willebrand Factor*, J. Biol. Chem., vol. 264, No. 33, 1989, pp. 19514-19527, Genebank Accession No. M25858.

Atsushi Nagai et al., *Analysis of the STR Loci HUMF13A01, HUMFXIIIB, HUMLIPOL. HUMTH01, HUMTPOX and HUMVWFA31 in a Japanese Population*, Int. J. Leg. Med, vol. 109, 1996, pp. 34-36.

Ann M. Lins et al., *Multiplex Sets for the Amplification of Polymorphic Short Tandem Repeat Loci—Silver Stain and Fluorescence Detection*, BioTechniques, vol. 20, No. 5, 1996, pp. 882-889.

Ronny Decorte et al., *Evaluation of the ALF DNA Sequencer for High-speed Sizing of Short Tandem Repeat Alleles*, Electrophoresis, vol. 17, 1996, pp. 1542-1549.

Jian Tie et al., *Analysis of STR Polymorphisms Using Capillary Gel Electrophoresis*, Res. Pract. Forens. Med., vol. 39, 1996, pp. 15-19, partial English translation.

I. W. Evett et al., *Statistical Analysis of Data for Three British Ethnic Groups from a New STR Multiplex*, Int. J. Leg. Med, vol. 110, 1997, pp. 5-9.

Peter Gill et al., *Considerations from the European DNA Profiling Group (EDNAP) Concerning STR Nomenclature*, Forensic Science International, vol. 87, 1997, pp. 185-192.

B. Rolf et al., *Automatische Analyse von Hoch Effizienten STRs*, Rechtsmedizin, vol. 7, 1997, pp. 157-161.

David E. O. Van Hoffstat et al., *Population Genetic Study of Four Short Tandem Repeat Loci in the Belgian Polulation, Using Capillary Electrophoresis*, Electrophoresis, vol. 19, 1998, pp. 719-722.

Feng-Xia Xiao et al., *Quadruplex Fluorescent STR Typing System (HUMVWA, HUMTH01, D21S11 and HPTR) with Sequence-defined Allelic Ladders Identification of a New Allele at D21S11*, Forensic Science International, vol. 94, 1998, pp. 39-46.

E. Mornhinweg et al., *D3S1358 and D8S1179: Analysis and Allele Frequencies in a South German Population*, Progress in Forensic Genetics 7, Proceedings of the 17th International ISFH Congress, Oslo, Sep. 1997, pp. 315-316.

Danuta Miscicka-Sliwka et al., *A Study of Sequence Polymorphism in Human Alpha Fibrinogen Gene in the Pomerania-Kujawy Region of Poland. Identification of a New Allele and Two Alleles Previously Reported to be Absent in Caucasians*, Progress in Forensic Genetics 7, Proceedings of the 17th International ISFH Congress, Oslo, Sep. 1997, pp. 384-386.

DNA Polymorphism, Chapter 3. *D12S76 D21S11 Locus*, vol. 6, Dec. 1997, no English translation.

DNA Polymorphism, Chapter 5. *PCT-SSCP TH01*, vol. 6, Dec. 1997, no English.

A. Moller, et al., *Different types of structural variation in STRs: HumFES/FPS, HumVWA and HumD21S11*, International Journal of Legal Medicine, vol. 106, 1994, pp. 319-323.

Christoph Puers et al., *Identification of Repeat Sequence Heterogeneity at the Polymorphic Short Tandem Repeat Locus HUMTH01[AATG]$_n$ and Reassignment of Alleles in Population Analysis by Using a Locus-specific Allelic Ladder*, American Journal Human Genetics, 53, 1993 pp. 953-958.

Colin Kimpton et al., *Report on the second EDNAP collaborative STR exercise*, Forensic Science International, vol. 71, 1995, pp. 137-152.

Florence Rousselet, et al., *A Pentaplex Automated Fluorescent Typing system for Forensic Identification and French Caucasian Population Data*, Journal of Forensic Sciences, vol. 42, No. 3, May 1997, pp. 500-503.

R.A.L. Griffiths, et al., *New reference allelic Ladders to improve allelic designation in a multiplex STR system*, International Journal of Legal Medicine, vol. 111, 1998. pp. 267-272.

D.J. Mancuso, et al., *Human von Willebrnad Factor Gene, Exon 39, 40, 31, and 42 and Alu repetitive element*, NCBI; Jan. 14, 1995, retrieved from http://www.ncbi.nlm.nih.gov, database accession No. M25858, XP002213448.

P. Gill, et al., *A new method of STR interpretation using inferential logic—development of a criminal intelligence database*, International Journal of Legal Medicine, vol. 109, 1996, pp. 14-22.

Barber et al., Intl. J. of Legal Medicine 109:62-65 (1996).

Budowie et al., Am J. of Human Genetics 48:137-144 (1991).

Edwards, et al., Am. J. of Human Genetics 49:746-756 (1991).

Kimpton et al., Electrophoresis 17:1283-1293 (1996).

Sharma et al., Human Molecular Genetics 1(1):67 (1992).

Sullivan et al., BioTechniques 15(4):636-641 (1993).

M.D. Barber et al., *Structural Variation in the Alleles of a Short Tandem Repeat System at the Human Alpha Fibrinogen Locus*, International Journal of Legal Medicine, vol. 108, 1996, pp. 180-185.

Peter Gill et al., *Considerations from the European DNA Profiling Group (EDNAP) Concerning STR Nomenclature*, Forensic Science International, vol. 87, 1997, pp. 185-192.

H-g. Zhou et al., *The HumD21S11 System of Short Tandem Repeat DNA Polymorphisms in Japanese and Chinese*, forensic Science International, vol. 86, 1997, pp. 109-118.

B. Brinkmann et al, *Complex Mutational Events at the HumD21S11 Locus*, Human Genetics, vol. 98, 1996, pp. 60-64.

Cecelia A. Crouse et al., *Investigation of Species Specificity Using Nine PCR-Based Human STR Systems*, Journal of Forensic Science, vol. 40, No. 6, Nov. 1995, pp. 952-956.

R. Sparkes et al., *The Validation of a 7-locus Multiplex STR Test for Use in Forensic Casework*, International Journal of Legal Medicine, vol. 109, 1996, pp. 195-204.

M.D. Barber, et al., *Structural Variation of Novel Alleles at the Hum vWA and Hum FES/FPS Short Tandem Repeat Loci*, International Journal of Medicine, vol. 108, 1995, pp. 31-35.

F. Rousselet et al., *French Caucasian Population Data Obtained from Fluorescently Detected HumvWFA31/A and HumF13A01 Short Tandem Repeat Loci*, International Journal of Medicine, vol. 109, 1996, pp. 5-9.

| loci | allelic designation | size (bp) | loci | allelic designation | size (bp) | loci | allelic designation | size (bp) | loci | allelic designation | size (bp) |
|---|---|---|---|---|---|---|---|---|---|---|---|
| TH01 | 4 | 150 | D8 | 7 | 157 | D18 | 8 | 266 | FGA (LMW) | 16.1 | 173 |
|  | 5 | 154 |  | 8 | 161 |  | 9 | 270 |  | 17 | 176 |
|  | 6 | 158 |  | 9 | 165 |  | 10 | 274 |  | 18 | 180 |
|  | 7 | 162 |  | 10 | 169 |  | 11 | 278 |  | 19 | 184 |
|  | 8 | 166 |  | 11 | 173 |  | 12 | 282 |  | 20 | 188 |
|  | 9 | 170 |  | 12 | 177 |  | 13 | 286 |  | 21 | 192 |
|  | 9.3 | 173 |  | 13 | 181 |  | 14 | 290 |  | 22 | 196 |
|  | 10 | 174 |  | 14 | 185 |  | 15 | 294 |  | 23 | 200 |
|  | 11 | 178 |  | 15 | 189 |  | 16 | 298 |  | 24 | 204 |
|  | 13.3 | 189 |  | 16 | 193 |  | 17 | 302 |  | 25 | 208 |
| D21 | 53 | 203 |  | 17 | 197 |  | 18 | 306 |  | 26 | 212 |
|  | 54 | 205 |  | 18 | 201 |  | 19 | 310 |  | 27 | 216 |
|  | 56 | 209 |  | 19 | 205 |  | 20 | 314 |  | 28 | 220 |
|  | 57 | 211 | VWA | 10 | 122 |  | 21 | 318 |  | 29 | 224 |
|  | 59 | 215 |  | 11 | 126 |  | 22 | 322 |  | 30 | 228 |
|  | 61 | 219 |  | 12 | 130 |  | 23 | 326 |  | 30.2 | 230 |
|  | 63 | 223 |  | 13 | 134 |  | 24 | 330 |  | 31.2 | 234 |

FIGURE 1A

| loci | allelic designation | size (bp) | loci | allelic designation | size (bp) | loci | allelic designation n | size (bp) |
|---|---|---|---|---|---|---|---|---|
|  | 65 | 227 |  | 14 | 138 |  | 25 | 334 |  | 32.2 | 238 |
|  | 67 | 231 |  | 15 | 142 |  | 26 | 338 |  | 33.2 | 242 |
|  | 68 | 233 |  | 16 | 146 | AMELO | 27 | 342 |  | 34.2 | 246 |
|  | 70 | 237 |  | 17 | 150 |  | X | 105 |  | 42.2 | 278 |
|  | 72 | 241 |  | 18 | 154 |  | Y | 111 |  | 42.3 | 282 |
|  | 74 | 245 |  | 19 | 158 |  |  |  |  | 44.2 | 286 |
|  | 75 | 247 |  | 20 | 162 |  |  |  |  | 45.2 | 290 |
|  | 77 | 251 |  | 21 | 166 |  |  |  |  | 46.2 | 294 |
|  | 79 | 255 |  |  |  |  |  |  |  | 47.2 | 298 |
|  | 81 | 259 |  |  |  |  |  |  |  | 48.2 | 302 |
|  |  |  |  |  |  |  |  |  |  | 50.2 | 310 |

FIGURE 1B

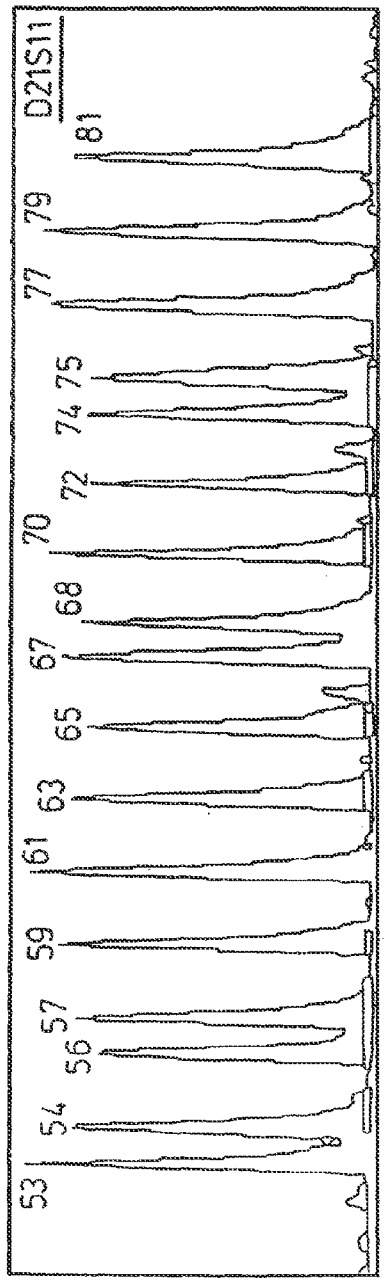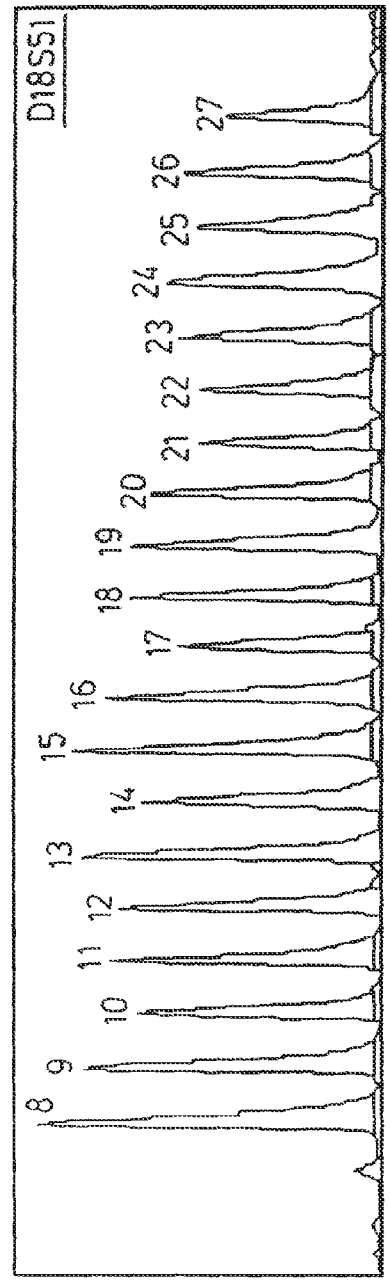
*FIGURE 2F*
*FIGURE 2G*

HUMVWAF31/A sequences                                        FIGURE 3A

10    TCTA TCTG TCTA (TCTG)$_4$ (TCTA)$_3$ (SEQ ID No: 1)

12    TCTA (TCTG)$_4$ (TCTA)$_7$ (SEQ ID No: 2)

13    (TCTA)$_2$ (TCTG)$_4$ (TCTA)$_3$ TCCA (TCTA)$_3$ (TCCA)$_2$ T (SEQ ID No: 39)

(Note also that the 13 allele has an atypical 3' flanking sequence (highlighted). The usual sequence is TCCA TCTA T.)

HUMTH01 sequences                                            FIGURE 3B

13.3  (TCAT)$_4$ CAT (TCAT)$_7$ TCGT$^{12th}$ TCAT (SEQ ID No: 4)

D8S1179 sequences                                            FIGURE 3C

7     (TCTA)$_8$, (SEQ ID No: 5)

19    (TCTA)$_2$ TCTG (TCTA)$_{16}$ (SEQ ID No: 6)

HUMFIBRA(FGA) Repeat Sequences                               FIGURE 3D

16.1  (TTTC)$_3$ TTTT TTCT (CTTT)$_5$ T (CTTT)$_3$ CTCC (TTCC)$_2$ (SEQ ID No: 7)

27    (TTTC)$_3$ TTTT TTCT (CTTT)$_{13}$ CCTT (CTTT)$_5$ CTCC (TTCC)$_2$ (SEQ ID No: 8)

30    (TTTC)$_3$ TTTT TTCT (CTTT)$_{16}$ CCTT (CTTT)$_5$ CTCC (TTCC)$_2$ (SEQ ID No: 9)

31.2  (TTTC)$_4$ TTTT TT (CTTT)$_{15}$ (CTTC)$_3$ (CTTT)$_3$ CTCC (TTCC)$_4$ (SEQ ID No: 10)

32.2  (TTTC)$_4$ TTTT TT (CTTT)$_{16}$ (CTTC)$_3$ (CTTT)$_3$ CTCC (TTCC)$_4$ (SEQ ID No: 11)

33.2  (TTTC)$_4$ TTTT TT (CTTT)$_{17}$ (CTTC)$_3$ (CTTT)$_3$ CTCC (TTCC)$_4$ (SEQ ID No: 12)

42.2  (TTTC)$_4$ TTTT TT (CTTT)$_8$ (CTGT)$_4$ (CTTT)$_{13}$ (CTTC)$_4$ (CTTT)$_3$ CTCC (TTCC)$_4$ (SEQ ID No: 13)

43.2  (TTTC)$_4$ TTTT TT (CTTT)$_8$ (CTGT)$_5$ (CTTT)$_{13}$ (CTTC)$_4$ (CTTT)$_3$ CTCC (TTCC)$_4$ (SEQ ID No: 14)

44.2  (TTTC)$_4$ TTTT TT (CTTT)$_{11}$ (CTGT)$_3$ (CTTT)$_{14}$ (CTTC)$_3$ (CTTT)$_3$ CTCC (TTCC)$_4$ (SEQ ID No: 15)

45.2  (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ (SEQ ID No: 16)

47.2  (TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ (SEQ ID No: 17)

48.2  (TTTC)$_4$ TTTT TT (CTTT)$_{14}$ (CTGT)$_3$ (CTTT)$_{14}$ (CTTC)$_4$ (CTTT)$_3$ CTCC (TTCC)$_4$ (SEQ ID No: 18)

D21S11 alleles                                                         FIGURE 3E 53    (TCTA)₄ (TCTG)₆ (TCTA)₃ TA(TCTA)₃ TCA (TCTA)₂ TCCATA
      (TCTA)₆ TCGTCT (SEQ ID No: 19)
54    (TCTA)₅ (TCTG)₆ (TCTA)₃ TCA (TCTA)₂ TCCATA (TCTA)₉ TCGTCT (SEQ ID No: 20)
56    (TCTA)₅ (TCTG)₆ (TCTA)₃ TCA (TCTA)₂ TCCATA (TCTA)₁₀ TCGTCT (SEQ ID No: 21)
57    (TCTA)₄ (TCTG)₆ (TCTA)₃ TA (TCTA)₃ TCA (TCTA)₂ TCCATA
      (TCTA)₈ TCGTCT (SEQ ID No: 22)
59    (TCTA)₅ (TCTG)₅ (TCTA)₃ TA (TCTA)₃ TCA (TCTA)₂ TCCATA
      (TCTA)₆ TCGTCT (SEQ ID No: 23)
61    (TCTA)₄ (TCTG)₆ (TCTA)₃ TA (TCTA)₃ TCA (TCTA)₂ TCCATA
      (TCTA)₁₀ TCGTCT (SEQ ID No: 24)
63    (TCTA)₄ (TCTG)₆ (TCTA)₃ TA (TCTA)₃ TCA (TCTA)₂ TCCATA
      (TCTA)₁₁ TCGTCT (SEQ ID No: 25)
65    (TCTA)₅ (TCTG)₅ (TCTA)₃ TA (TCTA)₃ TCA (TCTA)₂ TCCATA
      (TCTA)₁₁ TCGTCT (SEQ ID No: 26)
67    (TCTA)₅ (TCTG)₆ (TCTA)₃ TA (TCTA)₃ TCA (TCTA)₂ TCCATA
      (TCTA)₁₂ TCGTCT (SEQ ID No: 27)
68    (TCTA)₅ (TCTG)₆ (TCTA)₃ TA (TCTA)₃ TCA (TCTA)₂ TCCATA
      (TCTA)₁₁ TA TCTA TCGTCT (SEQ ID No: 28)
70    (TCTA)₅ (TCTG)₆ (TCTA)₃ TA (TCTA)₃ TCA (TCTA)₂ TCCATA
      (TCTA)₁₂ TA TCTA TCGTCT (SEQ ID No: 29)
72    (TCTA)₅ (TCTG)₆ (TCTA)₃ TA (TCTA)₃ TCA (TCTA)₂ TCCATA
      (TCTA)₁₃ TA TCTA TCGTCT (SEQ ID No: 30)
74    (TCTA)₅ (TCTG)₆ (TCTA)₃ TA (TCTA)₃ TCA (TCTA)₂ TCCATA
      (TCTA)₁₄ TATCTA TCGTCT (SEQ ID No: 31)
75    (TCTA)₁₀ (TCTG)₅ (TCTA)₃ TA (TCTA)₃ TCA (TCTA)₂ TCCATA
      (TCTA)₁₂ TCGTCT (SEQ ID No: 32)
77    (TCTA)₁₁ (TCTG)₅ (TCTA)₃ TA (TCTA)₃ TCA (TCTA)₂ TCCATA
      (TCTA)₁₂ TCGTCT (SEQ ID No: 33)
79    (TCTA)₁₁ (TCTG)₅ (TCTA)₃ TA (TCTA)₃ TCA (TCTA)₂ TCCATA
      (TCTA)₁₃ TCGTCT (SEQ ID No: 34)
81    (TCTA)₁₃ (TCTG)₅ (TCTA)₃ TA (TCTA)₃ TCA (TCTA)₂ TCCATA
      (TCTA)₁₂ TCGTCT (SEQ ID No: 35)

D18S51 sequences                                                       FIGURE 3F
8     (AGAA)₈ (SEQ ID No: 36)

```
                         SEQUENCE LISTING

<160> NUMBER OF SEQ ID NOS: 39

<210> SEQ ID NO 1
<211> LENGTH: 40
<212> TYPE: DNA
<213> ORGANISM: Homo sapiens

<400> SEQUENCE: 1
tctatctgtc tatctgtctg tctgtctgtc tatctatcta                          40

<210> SEQ ID NO 2
<211> LENGTH: 48
<212> TYPE: DNA
<213> ORGANISM: Homo sapiens

<400> SEQUENCE: 2
tctatctgtc tgtctgtctg tctatctatc tatctatcta tctatcta                 48

<210> SEQ ID NO 3
<211> LENGTH: 52
<212> TYPE: DNA
<213> ORGANISM: Homo sapiens

<400> SEQUENCE: 3
tctatctatc tgtctgtctg tctgtctatc tatctatcca tctatctatc ta            52

<210> SEQ ID NO 4
<211> LENGTH: 55
<212> TYPE: DNA
<213> ORGANISM: Homo sapiens

<400> SEQUENCE: 4
tcattcattc attcatcatt cattcattca ttcattcatt cattcattcg ttcat         55

<210> SEQ ID NO 5
<211> LENGTH: 32
<212> TYPE: DNA
<213> ORGANISM: Homo sapiens

<400> SEQUENCE: 5
tctatctatc tatctatcta tctatctatc ta                                  32

<210> SEQ ID NO 6
<211> LENGTH: 76
<212> TYPE: DNA
<213> ORGANISM: Homo sapiens

<400> SEQUENCE: 6
tctatctatc tgtctatcta tctatctatc tatctatcta tctatctatc tatctatcta    60
tctatctatc tatcta                                                    76

<210> SEQ ID NO 7
<211> LENGTH: 65
<212> TYPE: DNA
<213> ORGANISM: Homo sapiens

<400> SEQUENCE: 7
```

```
tttctttctt tctttttct ctttctttct ttctttcttt tctttcttc ttctccttc    60 cttcc                                                              65

<210> SEQ ID NO 8
<211> LENGTH: 108
<212> TYPE: DNA
<213> ORGANISM: Homo sapiens

<400> SEQUENCE: 8
tttctttctt tctttttct ctttctttct ttctttcttt ctttctttct ttctttcttt    60
ctttctttct ttccttcttt ctttctttct ttctttctcc ttccttcc              108

<210> SEQ ID NO 9
<211> LENGTH: 120
<212> TYPE: DNA
<213> ORGANISM: Homo sapiens

<400> SEQUENCE: 9
tttctttctt tctttttct ctttctttct ttctttcttt ctttctttct ttctttcttt    60
ctttctttct ttctttcttt ctttccttct ttctttcttt ctttctttct ccttccttcc  120

<210> SEQ ID NO 10
<211> LENGTH: 126
<212> TYPE: DNA
<213> ORGANISM: Homo sapiens

<400> SEQUENCE: 10
tttctttctt tctttctttt ttctttcttt ctttctttct ttctttcttt ctttctttct    60
ttctttcttt ctttctttct ttcttccttc ctccttcct ttctttctcc ttccttcctt  120
ccttcc                                                             126

<210> SEQ ID NO 11
<211> LENGTH: 130
<212> TYPE: DNA
<213> ORGANISM: Homo sapiens

<400> SEQUENCE: 11
tttctttctt tctttctttt ttctttcttt ctttctttct ttctttcttt ctttctttct    60
ttctttcttt ctttctttct ttctttcttc cttccttcct ttctttcttt ctccttcctt  120
ccttccttcc                                                         130

<210> SEQ ID NO 12
<211> LENGTH: 134
<212> TYPE: DNA
<213> ORGANISM: Homo sapiens

<400> SEQUENCE: 12
tttctttctt tctttctttt ttctttcttt ctttctttct ttctttcttt ctttctttct    60
ttctttcttt ctttctttct ttctttcttt ctccttcct tcctttcttt ctttctcctt  120
ccttccttcc ttcc                                                    134

<210> SEQ ID NO 13
<211> LENGTH: 170
<212> TYPE: DNA
<213> ORGANISM: Homo sapiens

<400> SEQUENCE: 13
```

```
tttctttctt tctttctttt ttctttcttt ctttctttct ttctttcttt ctttctgtct    60
gtctgtctgt ctttctttct ttctttcttt ctttctttct ttctttcttt ctttctttct   120
ttcttccttc cttccttcct ttctttcttt ctccttcctt ccttccttcc              170
```

<210> SEQ ID NO 14
<211> LENGTH: 174
<212> TYPE: DNA
<213> ORGANISM: Homo sapiens

<400> SEQUENCE: 14

```
tttctttctt tctttctttt ttctttcttt ctttctttct ttctttcttt ctttctgtct    60
gtctgtctgt ctgtctttct ttctttcttt ctttctttct ttctttcttt ctttctttct   120
ttctttcttc cttccttcct tcctttcttt ctttctcctt ccttccttcc ttcc         174
```

<210> SEQ ID NO 15
<211> LENGTH: 178
<212> TYPE: DNA
<213> ORGANISM: Homo sapiens

<400> SEQUENCE: 15

```
tttctttctt tctttctttt ttctttcttt ctttctttct ttctttcttt ctttctttct    60
ttctttctgt ctgtctgtct ttctttcttt ctttctttct ttctttcttt ctttctttct   120
ttctttcttt ctttcttcct tccttccttt ctttctttct ccttccttcc ttccttcc    178
```

<210> SEQ ID NO 16
<211> LENGTH: 182
<212> TYPE: DNA
<213> ORGANISM: Homo sapiens

<400> SEQUENCE: 16

```
tttctttctt tctttctttt ttctttcttt ctttctttct ttctttcttt ctttctttct    60
ttctgtctgt ctgtctgtct gtctttcttt ctttctttct ttctttcttt ctttctttct   120
ttctttcttt ctttcttcct tccttccttc ctttctttct ttctccttcc ttccttcctt   180
cc                                                                  182
```

<210> SEQ ID NO 17
<211> LENGTH: 190
<212> TYPE: DNA
<213> ORGANISM: Homo sapiens

<400> SEQUENCE: 17

```
tttctttctt tctttctttt ttctttcttt ctttctttct ttctttcttt ctttctttct    60
ttctttcttt ctgtctgtct gtctgtctgt ctttctttct ttctttcttt ctttctttct   120
ttctttcttt ctttctttct ttctttcttc cttccttcct ttctttcttt ctccttcctt   180
ccttccttcc                                                          190
```

<210> SEQ ID NO 18
<211> LENGTH: 194
<212> TYPE: DNA
<213> ORGANISM: Homo sapiens

<400> SEQUENCE: 18

```
tttctttctt tctttctttt ttctttcttt ctttctttct ttctttcttt ctttctttct    60
ttctttcttt ctttctttct gtctgtctgt ctttctttct ttctttcttt ctttctttct   120
ttctttcttt ctttctttct ttctttcttc cttccttcct tcctttcttt ctttctcctt   180
``` cttccttcc ttcc                                                    194

<210> SEQ ID NO 19
<211> LENGTH: 113
<212> TYPE: DNA
<213> ORGANISM: Homo sapiens

<400> SEQUENCE: 19
tctatctatc tatctatctg tctgtctgtc tgtctgtctg tctatctatc tatatctatc    60
tatctatcat ctatctatcc atatctatct atctatctat ctatctatcg tct          113

<210> SEQ ID NO 20
<211> LENGTH: 115
<212> TYPE: DNA
<213> ORGANISM: Homo sapiens

<400> SEQUENCE: 20
tctatctatc tatctatcta tctgtctgtc tgtctgtctg tctgtctatc tatctatcat    60
ctatctatcc atatctatct atctatctat ctatctatct atctatctat cgtct         115

<210> SEQ ID NO 21
<211> LENGTH: 119
<212> TYPE: DNA
<213> ORGANISM: Homo sapiens

<400> SEQUENCE: 21
tctatctatc tatctatcta tctgtctgtc tgtctgtctg tctgtctatc tatctatcat    60
ctatctatcc atatctatct atctatctat ctatctatct atctatctat ctatcgtct    119

<210> SEQ ID NO 22
<211> LENGTH: 121
<212> TYPE: DNA
<213> ORGANISM: Homo sapiens

<400> SEQUENCE: 22
tctatctatc tatctatctg tctgtctgtc tgtctgtctg tctatctatc tatatctatc    60
tatctatcat ctatctatcc atatctatct atctatctat ctatctatct atctatcgtc   120
t                                                                  121

<210> SEQ ID NO 23
<211> LENGTH: 125
<212> TYPE: DNA
<213> ORGANISM: Homo sapiens

<400> SEQUENCE: 23
tctatctatc tatctatcta tctgtctgtc tgtctgtctg tctatctatc tatatctatc    60
tatctatcat ctatctatcc atatctatct atctatctat ctatctatct atctatctat   120
cgtct                                                              125

<210> SEQ ID NO 24
<211> LENGTH: 129
<212> TYPE: DNA
<213> ORGANISM: Homo sapiens

<400> SEQUENCE: 24
tctatctatc tatctatctg tctgtctgtc tgtctgtctg tctatctatc tatatctatc    60
tatctatcat ctatctatcc atatctatct atctatctat ctatctatct atctatctat   120

-continued

| ctatcgtct | 129 |

<210> SEQ ID NO 25
<211> LENGTH: 133
<212> TYPE: DNA
<213> ORGANISM: Homo sapiens

<400> SEQUENCE: 25

| tctatctatc tatctatctg tctgtctgtc tgtctgtctg tctatctatc tatatctatc | 60 |
| tatctatcat ctatctatcc atatctatct atctatctat ctatctatct atctatctat | 120 |
| ctatctatcg tct | 133 |

<210> SEQ ID NO 26
<211> LENGTH: 137
<212> TYPE: DNA
<213> ORGANISM: Homo sapiens

<400> SEQUENCE: 26

| tctatctatc tatctatcta tctatctgtc tgtctgtctg tgtctgtatc tatctatatc | 60 |
| tatctatcta tcatctatct atccatatct atctatctat ctatctatct atctatctat | 120 |
| ctatctatct atcgtct | 137 |

<210> SEQ ID NO 27
<211> LENGTH: 141
<212> TYPE: DNA
<213> ORGANISM: Homo sapiens

<400> SEQUENCE: 27

| tctatctatc tatctatcta tctgtctgtc tgtctgtctg tctgtctatc tatctatatc | 60 |
| tatctatcta tcatctatct atccatatct atctatctat ctatctatct atctatctat | 120 |
| ctatctatct atctatcgtc t | 141 |

<210> SEQ ID NO 28
<211> LENGTH: 143
<212> TYPE: DNA
<213> ORGANISM: Homo sapiens

<400> SEQUENCE: 28

| tctatctatc tatctatcta tctgtctgtc tgtctgtctg tctgtctatc tatctatatc | 60 |
| tatctatcta tcatctatct atccatatct atctatctat ctatctatct atctatctat | 120 |
| ctatctatct atatctatcg tct | 143 |

<210> SEQ ID NO 29
<211> LENGTH: 147
<212> TYPE: DNA
<213> ORGANISM: Homo sapiens

<400> SEQUENCE: 29

| tctatctatc tatctatcta tctgtctgtc tgtctgtctg tctgtctatc tatctatatc | 60 |
| tatctatcta tcatctatct atccatatct atctatctat ctatctatct atctatctat | 120 |
| ctatctatct atctatatct atcgtct | 147 |

<210> SEQ ID NO 30
<211> LENGTH: 151
<212> TYPE: DNA
<213> ORGANISM: Homo sapiens

<400> SEQUENCE: 30

-continued

```
tctatctatc tatctatcta tctgtctgtc tgtctgtctg tctgtctatc tatctatatc        60
tatctatcta tcatctatct atccatatct atctatctat ctatctatct atctatctat       120
ctatctatct atctatctat atctatcgtc t                                      151

<210> SEQ ID NO 31
<211> LENGTH: 155
<212> TYPE: DNA
<213> ORGANISM: Homo sapiens

<400> SEQUENCE: 31
tctatctatc tatctatcta tctgtctgtc tgtctgtctg tctgtctatc tatctatatc        60
tatctatcta tcatctatct atccatatct atctatctat ctatctatct atctatctat       120
ctatctatct atctatctat ctatatctat cgtct                                  155

<210> SEQ ID NO 32
<211> LENGTH: 157
<212> TYPE: DNA
<213> ORGANISM: Homo sapiens

<400> SEQUENCE: 32
tctatctatc tatctatcta tctatctatc tatctatcta tctgtctgtc tgtctgtctg        60
tctatctatc tatatctatc tatctatcat ctatctatcc atatctatct atctatctat       120
ctatctatct atctatctat ctatctatct atcgtct                                157

<210> SEQ ID NO 33
<211> LENGTH: 161
<212> TYPE: DNA
<213> ORGANISM: Homo sapiens

<400> SEQUENCE: 33
tctatctatc tatctatcta tctatctatc tatctatcta tctatctgtc tgtctgtctg        60
tctgtctatc tatctatatc tatctatcta tcatctatct atccatatct atctatctat       120
ctatctatct atctatctat ctatctatct atctatcgtc t                           161

<210> SEQ ID NO 34
<211> LENGTH: 165
<212> TYPE: DNA
<213> ORGANISM: Homo sapiens

<400> SEQUENCE: 34
tctatctatc tatctatcta tctatctatc tatctatcta tctatctgtc tgtctgtctg        60
tctgtctatc tatctatatc tatctatcta tcatctatct atccatatct atctatctat       120
ctatctatct atctatctat ctatctatct atctatctat cgtct                       165

<210> SEQ ID NO 35
<211> LENGTH: 169
<212> TYPE: DNA
<213> ORGANISM: Homo sapiens

<400> SEQUENCE: 35
tctatctatc tatctatcta tctatctatc tatctatcta tctatctatc tatctgtctg        60
tctgtctgtc tgtctatcta tctatatcta tctatctatc atctatctat ccatatctat       120
ctatctatct atctatctat ctatctatct atctatctat ctatcgtct                  169

<210> SEQ ID NO 36
```

-continued

```
<211> LENGTH: 32
<212> TYPE: DNA
<213> ORGANISM: Homo sapiens

<400> SEQUENCE: 36
agaaagaaag aaagaaagaa agaaagaaag aa                                    32

<210> SEQ ID NO 37
<211> LENGTH: 14
<212> TYPE: DNA
<213> ORGANISM: Homo sapiens

<400> SEQUENCE: 37
tatctatcta tcta                                                        14

<210> SEQ ID NO 38
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: This sequence may encompass 8 to 27 'AGAA'
      repeating units

<400> SEQUENCE: 38
agaaagaaag aaagaaagaa agaaagaaag aaagaaagaa agaaagaaag aaagaaagaa       60
agaaagaaag aaagaaagaa agaaagaaag aaagaaagaa agaaagaa                   108

<210> SEQ ID NO 39
<211> LENGTH: 65
<212> TYPE: DNA
<213> ORGANISM: Homo sapiens

<400> SEQUENCE: 39
tctatctatc tgtctgtctg tctgtctatc tatctatcca tctatctatc tatccatcca       60
tccat                                                                  65
```

FORENSIC IDENTIFICATION

CROSS-REFERENCE TO RELATED APPLICATIONS

This application is a continuation of U.S. patent application Ser. No. 11/244,331, filed Oct. 4, 2005, which is a continuation of U.S. patent application Ser. No. 09/910,183, filed Jul. 20, 2001, now U.S. Pat. No. 7,087,380, issued Aug. 8, 2006, which is a continuation of U.S. patent application Ser. No. 09/706,525, filed Nov. 3, 2000 (abandoned), which is a continuation of U.S. patent application Ser. No. 09/498,567, filed Feb. 4, 2000 (abandoned), which is a continuation of U.S. patent application Ser. No. 09/107,029, filed Jun. 29, 1998 (abandoned), which claims priority to United Kingdom Application No. 9713597.4, filed Jun. 28, 1997, which for purposes of disclosure are incorporated herein by specific reference.

BACKGROUND OF THE INVENTION

1. The Field of the Invention

The present invention is concerned with improvements in and relating to forensic identification, particularly where based on DNA profiling.

2. The Relevant Technology

DNA profiling offers a versatile identification technique for a wide variety of applications including, anthropological, paternity and other forensic environments. The use of such profiling is significant in determining, links, or their absence, between samples. Such samples might include those taken from known individuals and/or those taken from the scene of or linked to a crime.

DNA profiling based on the use of short tandem repeats (STR) or micro satellite loci is used in such applications. STR's are a class of polymorphic markers which consist of simple tandomly repeated sequences of between 1 and 6 base pairs in length. STR's in the non-coding part of the genome are generally considered.

In the human genome STR's occur every 6 to 10 kilo bases along the DNA. The length, however, varies greatly between individuals due to mutation and provides identifying characteristics as a result.

A variety of DNA profiling systems exist, including single locus analysis and multiple locus analysis where a number of STR loci are simultaneously amplified.

In analysing the results from an unknown sample it is generally considered against a ladder marker consisting of alleles derived from actual samples. The allelic ladder provides a reference point and allows correspondence of alleles to be identified clearly.

SUMMARY OF THE INVENTION

The present invention provides new alleles and new ladders incorporating them for a variety of loci. The present invention offers an improved range and coverage of markers as a result. The ladders include a number of rare alleles offering improved identification of the alleles in an unknown sample.

According to a first aspect of the invention we provide an allelic ladder mixture comprising one or more of the following allelic ladders:

i) an allelic ladder for locus HUMVWFA31/A comprising one or more of alleles comprising or consisting of sequences:

TCTA TCTG TCTA $(TCTG)_4$ $(TCTA)_3$; (SEQ ID NO: 1)

TCTA $(TCTG)_4$ $(TCTA)_7$; or (SEQ ID NO: 2)

$(TCTA)_2$ $(TCTG)_4$ $(TCTA)_3$ TCCA $(TCTA)_3$ (SEQ ID NO: 3)

or at least 75% homologous thereto;

ii) an allelic ladder for locus HUMTHO1 comprising or consisting of sequence:

$(TCAT)_4$ CAT $(TCAT)_7$ TCGT TCAT; (SEQ ID NO: 4)

or at least 75% homologous thereto;

iii) an allelic ladder for locus D8S1179 comprising one or more of alleles:

$(TCTA)_8$; (SEQ ID NO: 5)

$(TCTA)_2$ TCTG$(TCTA)_{16}$ (SEQ ID NO: 6)

or at least 75% homologous thereto;

iv) an allelic ladder for locus HUMFIBRA/FGA comprising one or more of alleles comprising or consisting of the sequences:

(SEQ ID NO: 7)
$(TTTC)_3$ TTTT TTCT $(CTTT)_5$ T $(CTTT)_3$ CTCC $(TTCC)_2$;

(SEQ ID NO: 8)
$(TTTC)_3$ TTTT TTCT $(CTTT)_{13}$ CCTT $(CTTT)_5$ CTCC $(TTCC)_2$;

(SEQ ID NO: 9)
$(TTTC)_3$ TTTT TTCT $(CTTT)_{16}$ CCTT $(CTTT)_5$ CTCC $(TTCC)_2$;

(SEQ ID NO: 10)
$(TTTC)_4$ TTTT TT $(CTTT)_{15}$ $(CTTC)_3$ $(CTTT)_3$ CTCC $(TTCC)_4$;

(SEQ ID NO: 11)
$(TTTC)_4$ TTTT TT $(CTTT)_{16}$ $(CTTC)_3$ $(CTTT)_3$ CTCC $(TTCC)_4$;

(SEQ ID NO: 12)
$(TTTC)_4$ TTTT TT $(CTTT)_{17}$ $(CTTC)_3$ $(CTTT)_3$ CTCC $(TTCC)_4$;

(SEQ ID NO: 13)
$(TTTC)_4$ TTTT TT $(CTTT)_8$ $(CTGT)_4$ $(CTTT)_{13}$ $(CTTC)_4$ $(CTTT)_3$ CTCC $(TTCC)_4$;

(SEQ ID NO: 14)
$(TTTC)_4$ TTTT TT $(CTTT)_8$ $(CTGT)_5$ $(CTTT)_{13}$ $(CTTC)_4$ $(CTTT)_3$ CTCC $(TTCC)_4$;

(SEQ ID NO: 15)
$(TTTC)_4$ TTTT TT $(CTTT)_{11}$ $(CTGT)_3$ $(CTTT)_{14}$ $(CTTC)_3$ $(CTTT)_3$ CTCC $(TTCC)_4$;

(SEQ ID NO: 16)
$(TTTC)_4$ TTTT TT $(CTTT)_{10}$ $(CTGT)_5$ $(CTTT)_{13}$ $(CTTC)_4$

-continued (CTTT)$_3$ CTCC (TTCC)$_4$;

(SEQ ID NO: 17)
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$; or (SEQ ID NO: 18)
(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$;

or at least 75% homologous thereto;

v) al allelic ladder for locus D21S11 comprising one or more of alleles comprising or consisting of sequences:

| | |
|---|---|
| (TCTA)$_4$ (TCTG)$_6$ (TCTA)$_3$ TA(TCTA)$_3$ TCA (TCTA)$_2$ TCCATA (TCTA)$_6$ TCGTCT | (SEQ ID NO: 19); |
| (TCTA)$_5$ (TCTG)$_6$ (TCTA)$_3$ TCA (TCTA)$_2$ TCCATA (TCTA)$_9$ TCGTCT | (SEQ ID NO: 20); |
| (TCTA)$_5$ (TCTG)$_6$ (TCTA)$_3$ TCA (TCTA)$_2$ TCCATA (TCTA)$_{10}$ TCGTCT | (SEQ ID NO: 21); |
| (TCTA)$_4$ (TCTG)$_6$ (TCTA)$_3$ TA (TCTA)$_3$ TCA (TCTA)$_2$ TCCATA (TCTA)$_8$ TCGTCT | (SEQ ID NO: 22); |
| (TCTA)$_5$ (TCTG)$_5$ (TCTA)$_3$ TA (TCTA)$_3$ TCA (TCTA)$_2$ TCCATA (TCTA)$_9$ TCGTCT | (SEQ ID NO: 23); |
| (TCTA)$_4$ (TCTG)$_6$ (TCTA)$_3$ TA (TCTA)$_3$ TCA (TCTA)$_2$ TCCATA (TCTA)$_{10}$ TCGTCT | (SEQ ID NO: 24); |
| (TCTA)$_4$ (TCTG)$_6$ (TCTA)$_3$ TA (TCTA)$_3$ TCA (TCTA)$_2$ TCCATA (TCTA)$_{11}$ TCGTCT | (SEQ ID NO: 25); |
| (TCTA)$_6$ (TCTG)$_5$ (TCTA)$_3$ TA (TCTA)$_3$ TCA (TCTA)$_2$ TCCATA (TCTA)$_{11}$ TCGTCT | (SEQ ID NO: 26); |
| (TCTA)$_5$ (TCTG)$_6$ (TCTA)$_3$ TA (TCTA)$_3$ TCA (TCTA)$_2$ TCCATA (TCTA)$_{12}$ TCGTCT | (SEQ ID NO: 27); |
| (TCTA)$_5$ (TCTG)$_6$ (TCTA)$_3$ TA (TCTA)$_3$ TCA (TCTA)$_2$ TCCATA (TCTA)$_{11}$ TA TCTA TCGTCT | (SEQ ID NO: 28); |
| (TCTA)$_5$ (TCTG)$_6$ (TCTA)$_3$ TA (TCTA)$_3$ TCA (TCTA)$_3$ TCCATA (TCTA)$_{12}$ TA TCTA TCGTCT | (SEQ ID NO: 29); |
| (TCTA)$_5$ (TCTG)$_6$ (TCTA)$_3$ TA (TCTA)$_3$ TCA (TCTA)$_2$ TCCATA (TCTA)$_{13}$ TA TCTA TCGTCT | (SEQ ID NO: 30); |
| (TCTA)$_5$ (TCTG)$_6$ (TCTA)$_3$ TA (TCTA)$_3$ TCA (TCTA)$_2$ TCCATA (TCTA)$_{14}$ TATCTA TCGTCT | (SEQ ID NO: 31); |
| (TCTA)$_{10}$ (TCTG)$_5$ (TCTA)$_3$ TA (TCTA)$_3$ TCA (TCTA)$_2$ TCCATA (TCTA)$_{12}$ TCGTCT | (SEQ ID NO: 32); |
| (TCTA)$_{11}$ (TCTG)$_5$ (TCTA)$_3$ TA (TCTA)$_3$ TCA (TCTA)$_2$ TCCATA (TCTA)$_{12}$ TCGTCT | (SEQ ID NO: 33); |
| (TCTA)$_{11}$ (TCTG)$_5$ (TCTA)$_3$ TA (TCTA)$_3$ TCA (TCTA)$_2$ TCCATA (TCTA)$_{13}$ TCGTCT | (SEQ ID NO: 34); or |
| (TCTA)$_{13}$ (TCTG)$_5$ (TCTA)$_3$ TA (TCTA)$_3$ TCA (TCTA)$_2$ TCCATA (TCTA)$_{12}$ TCGTCT | (SEQ ID NO: 35); | or at least 75% homologous thereto;

vi) an allelic ladder for locus D18S51 comprising an allele comprising or consisting of sequence:

| | |
|---|---|
| (AGAA)$_8$ | (SEQ ID NO: 36); | or at least 75% homologous thereto.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTHO1, D8S1179, HUMFIBRA/FGA, D21S11 and D18S51. Preferably the mixture includes allelic ladders for at least four of these loci. In its most preferred form the mixture includes allelic ladders for all of these loci.

Preferably the mixture includes an amelogenin sex test.

Preferably one or more of the allelic ladders in the mixture includes at least 7 alleles and more preferably at least 12 alleles. Preferably a plurality, and particularly all, of the allelic ladders of the mixture include at least 8 and more preferably at least 10 alleles.

Preferably one or more or all of the ladders, if present in the mixture, may be provided such that: the HUMVWFA31/A allelic ladder includes at least 9, more preferably 11 and ideally 12 alleles; the HUMTHO1 allelic ladder includes at least 7, more preferably 9 and ideally 10 alleles; the D8S1179 allelic ladder includes at least 9, more preferably 12 and ideally 13 alleles; the HUMFIBRA/FGA allelic ladder includes at least 18, more preferably 26 and ideally 28 alleles or is present as HUMFIBRA/FGA/LW and HUMFIBRA/FGA/HW with the HUMFIBRA/FGA/LW ladder including at least 16 more preferably 18 and ideally 20 alleles, the HUMFIBRA/FGA/HW ladder including at least 6, more preferably at least 7 and ideally 8 alleles; the D21S11 allelic ladder includes at least 14, more preferably 16 and ideally 17 alleles; and the D18S51 ladder includes at least 15, more preferably 19 and ideally 20 alleles.

Preferably one or more of the allelic ladders in the mixture comprises at least 4 pairs of alleles 4 base pairs from each other. More preferably at least 10 pairs, and ideally at least 12 pairs of alleles are so provided. Preferably one or more or all the allelic ladders, if present in the mixture, may be provided such that: the HUMVWFA31/A allelic ladder includes at least 7, more preferably 10 and ideally 11 pairs of alleles 4 base pairs from each other; the HUMTHO1 allelic ladder includes at least 5, more preferably 6 and ideally 7 pairs of alleles 4 base pairs from each other; the D8S1179 allelic ladder includes at least 8, more preferably 11 and ideally 12 pairs of alleles 4 base pairs from each other; the HUMFIBRA/FGA allelic ladder includes at least 17, more preferably 20 and ideally 23 pairs of alleles 4 base pairs from each other; the D21S11 allelic ladder includes at least 3 and ideally 4 pairs of alleles 4 base pairs from each other; and the D18S51 ladder includes at least 13, more preferably 18 and ideally 19 pairs of alleles 4 base pairs from each other. The D21S11 allelic ladder may, or may further include, at least 8, more preferably 11 and ideally 12 pairs of alleles 8 base pairs from each other.

Preferably the allele sequences have at least 85% homogeneity with the listed sequences. More preferable levels of even 90% or at least 95% may be provided. Ideally the exact sequences listed are included within the alleles. In their most preferred form the alleles consist of the listed sequences.

The alleles may further include flanking sequences, i.e., between the primer and STR.

Preferably the HUMVWFA31/A ladder includes alleles ranging from 130, more preferably 126 and ideally 122 base pairs upwards and/or from 166 base pairs downwards. Preferably the HUMTH01 ladder includes alleles ranging from 150 base pairs upwards and/or 189 base pairs downwards. Preferably the D8S1179 ladder includes alleles ranging from 157 base pairs upwards and/or 201, and more preferably 205 base pairs downwards. Preferably the HUMFIBRA/FGA ladder includes alleles ranging from 173 base pairs upwards and/or 298, more preferably 302 and ideally 310 base pairs downwards. Preferably the D21S11 ladder includes alleles ranging from 203 base pairs upwards and/or 255 or more preferably 259 base pairs downwards. Preferably the D18S51 ladder includes alleles ranging from 270 or more preferably 266 base pairs upwards and/or 326 or 330 or 334 or 338 or even 342 downwards.

According to a second aspect of the invention we provide an allelic ladder mixture comprising an allelic ladder for one or more of the following loci, with lowest molecular weight allele and/or uppermost molecular weight allele as follows:

| Locus | Low MW allele | High MW allele |
| --- | --- | --- |
| a) HUMVWFA31/A | 10 | 21 |
| b) HUMTH01 | 4 | 13.3 |
| c) D8S1179 | 7 | 19 |
| d) HUMFIBRA/FGA | 16.1 | 50.2 |
| e) D21S11 | 53 | 81 |
| f) D18S51 | 8 | 27 |

Preferably one or more of the loci ladders have both the upper and lower limits specified. Preferably all the loci ladders have the full ranges listed.

Preferably the mixture includes allelic ladders for a plurality of loci. It is particularly preferred that the mixture include allelic ladders for at least four loci. Preferably the mixture includes allelic ladders for a plurality of loci selected from HUMVWFA31/A, HUMTH01, D8S1179, HUMFIBRA/FGA, D21S11 and D18S51. Preferably the mixture includes allelic ladders for at least four of these loci. In its most preferred form the mixture includes allelic ladders for all of these loci.

The intervals of alleles in the ladders and/or number of alleles in the ladders may be as specified in the first aspect of the invention. This aspect may include any of the other features specified elsewhere in the application.

The ladder mixtures of the first and/or second aspect of the invention may further include one or more of PARR buffer, primer(s), or Taq polymerase.

According to a third aspect of the invention we provide a method of analysing one or more samples comprising:

a) obtaining genomic DNA from the sample;

b) amplifying the DNA;

c) obtaining an indication of one or more of the constituent parts of the sample; and comparing the indications with an allelic ladder mixture comprising one or more of the following allelic ladders:

i) an allelic ladder for locus HUMVWFA31/A comprising one or more of alleles comprising or consisting of sequences:

TCTA TCTG TCTA $(TCTG)_4$ $(TCTA)_3$;        (SEQ ID NO: 1)

TCTA $(TCTG)_4$ $(TCTA)_7$; or        (SEQ ID NO: 2)

$(TCTA)_2$ $(TCTG)_4$ $(TCTA)_3$ TCCA $(TCTA)_3$        (SEQ ID NO: 3)

ii) an allelic ladder for locus HUMTH01 comprising or consisting of sequence:

$(TCAT)_4$ CAT $(TCAT)_7$ TCGT TCAT        (SEQ ID NO: 4);

iii) an allelic ladder for locus D8S1179 comprising one or more of alleles comprising or consisting of sequences:

$(TCTA)_8$        (SEQ ID NO: 5); or $(TCTA)_2$ TCTG $(TCTA)_{16}$        (SEQ ID NO: 6);

iv) an allelic ladder for locus HUMFIBRA/FGA comprising one or more of alleles comprising or consisting of the sequences:

$(TTTC)_3$ TTTT TTCT $(CTTT)_5$ T $(CTTT)_3$ CTCC $(TTCC)_2$        (SEQ ID NO: 7);

$(TTTC)_3$ TTTT TTCT $(CTTT)_{13}$ CCTT $(CTTT)_5$ CTCC $(TTCC)_2$        (SEQ ID NO: 8);

$(TTTC)_3$ TTTT TTCT $(CTTT)_{16}$ CCTT $(CTTT)_5$ CTCC $(TTCC)_2$        (SEQ ID NO: 9);

$(TTTC)_4$ TTTT TT $(CTTT)_{15}$ $(CTTC)_3$ $(CTTT)_3$ CTCC $(TTCC)_4$        (SEQ ID NO: 10);

$(TTTC)_4$ TTTT TT $(CTTT)_{16}$ $(CTTC)_3$ $(CTTT)_3$ CTCC $(TTCC)_4$        (SEQ ID NO: 11);

$(TTTC)_4$ TTTT TT $(CTTT)_{17}$ $(CTTC)_3$ $(CTTT)_3$ CTCC $(TTCC)_4$        (SEQ ID NO: 12);

$(TTTC)_4$ TTTT TT $(CTTT)_8$ $(CTGT)_4$ $(CTTT)_{13}$ $(CTTC)_4$ $(CTTT)_3$ CTCC $(TTCC)_4$        (SEQ ID NO: 13);

$(TTTC)_4$ TTTT TT $(CTTT)_8$ $(CTGT)_5$ $(CTTT)_{13}$ $(CTTC)_4$ $(CTTT)_3$ CTCC $(TTCC)_4$        (SEQ ID NO: 14);

$(TTTC)_4$ TTTT TT $(CTTT)_{11}$ $(CTGT)_3$ $(CTTT)_{14}$ $(CTTC)_3$ $(CTTT)_3$ CTCC $(TTCC)_4$        (SEQ ID NO: 15);

-continued (TTTC)$_4$ TTTT TT (CTTT)$_{10}$ (CTGT)$_5$ (CTTT)$_{13}$ (CTTC)$_4$ (CTTT)$_3$ CTCC (TTCC)$_4$ (SEQ ID NO: 16);

(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$ (SEQ ID NO: 17); or (TTTC)$_4$ TTTT TT (CTTT)$_{14}$ (CTGT)$_3$ (CTTT)$_{14}$ (CTTC)$_4$ (CTTT)$_3$ CTCC (TTCC)$_4$ (SEQ ID NO: 18);

v) an allelic ladder for locus D21S11 comprising one or more of alleles comprising or consisting of sequences:

(TCTA)$_4$ (TCTG)$_6$ (TCTA)$_3$ TA(TCTA)$_3$ TCA (TCTA)$_2$ TCCATA (TCTA)$_6$ TCGTCT (SEQ ID NO: 19);

(TCTA)$_5$ (TCTG)$_6$ (TCTA)$_3$ TCA (TCTA)$_2$ TCCATA (TCTA)$_9$ TCGTCT (SEQ ID NO: 20);

(TCTA)$_5$ (TCTG)$_6$ (TCTA)$_3$ TCA (TCTA)$_2$ TCCATA (TCTA)$_{10}$ TCGTCT (SEQ ID NO: 21);

(TCTA)$_4$ (TCTG)$_6$ (TCTA)$_3$ TA (TCTA)$_3$ TCA (TCTA)$_2$ TCCATA (TCTA)$_8$ TCGTCT (SEQ ID NO: 22);

(TCTA)$_5$ (TCTG)$_5$ (TCTA)$_3$ TA (TCTA)$_3$ TCA (TCTA)$_2$ TCCATA (TCTA)$_9$ TCGTCT (SEQ ID NO: 23);

(TCTA)$_4$ (TCTG)$_6$ (TCTA)$_3$ TA (TCTA)$_3$ TCA (TCTA)$_2$ TCCATA (TCTA)$_{10}$ TCGTCT (SEQ ID NO: 24);

(TCTA)$_4$ (TCTG)$_6$ (TCTA)$_3$ TA (TCTA)$_3$ TCA (TCTA)$_2$ TCCATA (TCTA)$_{11}$ TCGTCT (SEQ ID NO: 25);

(TCTA)$_6$ (TCTG)$_5$ (TCTA)$_3$ TA (TCTA)$_3$ TCA (TCTA)$_2$ TCCATA (TCTA)$_{11}$ TCGTCT (SEQ ID NO: 26);

(TCTA)$_5$ (TCTG)$_6$ (TCTA)$_3$ TA (TCTA)$_3$ TCA (TCTA)$_2$ TCCATA (TCTA)$_{12}$ TCGTCT (SEQ ID NO: 27);

(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT (SEQ ID NO: 28);

(TCTA)$_5$ (TCTG)$_6$ (TCTA)$_3$ TA (TCTA)$_3$ TCA (TCTA)$_2$ TCCATA (TCTA)$_{12}$ TA TCTA TCGTCT (SEQ ID NO: 29);

(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT (SEQ ID NO: 30);

(TCTA)$_5$ (TCTG)$_6$ (TCTA)$_3$ TA (TCTA)$_3$ TCA (TCTA)$_2$ TCCATA (TCTA)$_{14}$ TATCTA TCGTCT (SEQ ID NO: 31);

(TCTA)$_{10}$ (TCTG)$_5$ (TCTA)$_3$ TA (TCTA)$_3$ TCA (TCTA)$_2$ TCCATA (TCTA)$_{12}$ TCGTCT (SEQ ID NO: 32);

(TCTA)$_{11}$ (TCTG)$_5$ (TCTA)$_3$ TA (TCTA)$_3$ TCA (TCTA)$_2$ TCCATA (TCTA)$_{12}$ TCGTCT (SEQ ID NO: 33);

(TCTA)$_{11}$ (TCTG)$_5$ (TCTA)$_3$ TA (TCTA)$_3$ TCA (TCTA)$_2$ TCCATA (TCTA)$_{13}$ TCGTCT (SEQ ID NO: 34); or (TCTA)$_{13}$ (TCTG)$_5$ (TCTA)$_3$ TA (TCTA)$_3$ TCA (TCTA)$_2$ TCCATA (TCTA)$_{12}$ TCGTCT (SEQ ID NO: 35);

vi) an allelic ladder for locus D18S51 comprising an allele comprising or consisting of sequence:

(AGAA)$_8$ (SEQ ID NO: 36);

including allelic ladders or alleles 75% homologous thereto.

The allelic ladder mixture may possess other features specified in the first or second aspects of the invention or elsewhere in this application.

Preferably the DNA sample is one or more of a sample taken from the scene of a crime, a sample associated with the scene of a crime, a sample obtained from a suspect, a sample obtained from a human under consideration (for instance for paternity or maternity analysis) or a reference sample. The sample may be in the form of blood, hair, skin or bodily fluid.

Preferably the sample is amplified using a polymerase chain reaction. Preferably primers for one or more of loci HUMVWFA31/A, HUMTHO1, D8S1179, HUMFIBRA/FGA, D21S11 or D18S51 are employed. The primers may be dye or otherwise labelled.

According to a fourth aspect of the invention we provide one or more alleles comprising or consisting of sequences:

TCTA TCTG TCTA (TCTG)$_4$ (TCTA)$_3$; (SEQ ID NO: 1)

TCTA (TCTG)$_4$ (TCTA)$_7$; (SEQ ID NO: 2)

(TCTA)$_2$ (TCTG)$_4$ (TCTA)$_3$ TCCA (TCTA)$_3$; (SEQ ID NO: 3)

(TCAT)$_4$ CAT (TCAT)$_7$ TCGT TCAT; (SEQ ID NO: 4)

(TCTA)$_8$; (SEQ ID NO: 5)

(TCTA)$_2$ TCTG (TCTA)$_{16}$; (SEQ ID NO: 6)

(SEQ ID NO: 7)
(TTTC)$_3$ TTTT TTCT (CTTT)$_5$ T (CTTT)$_3$ CTCC (TTCC)$_2$;

(SEQ ID NO: 8)
(TTTC)$_3$ TTTT TTCT (CTTT)$_{13}$ CCTT (CTTT)$_5$ CTCC (TTCC)$_2$;

(SEQ ID NO: 9)
(TTTC)$_3$ TTTT TTCT (CTTT)$_{16}$ CCTT (CTTT)$_5$ CTCC (TTCC)$_2$;

-continued (SEQ ID NO: 10)
(TTTC)$_4$ TTTT TT (CTTT)$_{15}$ (CTTC)$_3$ (CTTT)$_3$ CTCC (TTCC)$_4$;

(SEQ ID NO: 11)
(TTTC)$_4$ TTTT TT (CTTT)$_{16}$ (CTTC)$_3$ (CTTT)$_3$ CTCC (TTCC)$_4$;

(SEQ ID NO: 12)
(TTTC)$_4$ TTTT TT (CTTT)$_{17}$ (CTTC)$_3$ (CTTT)$_3$ CTCC (TTCC)$_4$;

(SEQ ID NO: 13)
(TTTC)$_4$ TTTT TT (CTTT)$_8$ (CTGT)$_4$ (CTTT)$_{13}$ (CTTC)$_4$ (CTTT)$_3$ CTCC (TTCC)$_4$;

(SEQ ID NO: 14)
(TTTC)$_4$ TTTT TT (CTTT)$_8$ (CTGT)$_5$ (CTTT)$_{13}$ (CTTC)$_4$ (CTTT)$_3$ CTCC (TTCC)$_4$;

(SEQ ID NO: 15)
(TTTC)$_4$ TTTT TT (CTTT)$_{11}$ (CTGT)$_3$ (CTTT)$_{14}$ (CTTC)$_3$ (CTTT)$_3$ CTCC (TTCC)$_4$;

(SEQ ID NO: 16)
(TTTC)$_4$ TTTT TT (CTTT)$_{10}$ (CTGT)$_5$ (CTTT)$_{13}$ (CTTC)$_4$ (CTTT)$_3$ CTCC (TTCC)$_4$;

(SEQ ID NO: 17)
(TTTC)$_4$ TTTT TT (CTTT)$_{12}$ (CTGT)$_5$ (CTTT)$_{14}$ (CTTC)$_3$ (CTTT)$_3$ CTCC (TTCC)$_4$;

(SEQ ID NO: 18)
(TTTC)$_4$ TTTT TT (CTTT)$_{14}$ (CTGT)$_3$ (CTTT)$_{14}$ (CTTC)$_4$ (CTTT)$_3$ CTCC (TTCC)$_4$;

(SEQ ID NO: 19)
(TCTA)$_4$ (TCTG)$_6$ (TCTA)$_3$ TA(TCTA)$_3$ TCA (TCTA)$_2$ TCCATA (TCTA)$_6$ TCGTCT;

(SEQ ID NO: 20)
(TCTA)$_5$ (TCTG)$_6$ (TCTA)$_3$ TCA (TCTA)$_2$ TCCATA (TCTA)$_9$ TCGTCT;

(SEQ ID NO: 21)
(TCTA)$_5$ (TCTG)$_6$ (TCTA)$_3$ TCA (TCTA)$_2$ TCCATA (TCTA)$_{10}$ TCGTCT;

(SEQ ID NO: 22)
(TCTA)$_4$ (TCTG)$_6$ (TCTA)$_3$ TA (TCTA)$_3$ TCA (TCTA)$_2$ TCCATA (TCTA)$_8$ TCGTCT;

(SEQ ID NO: 23)
(TCTA)$_5$ (TCTG)$_5$ (TCTA)$_3$ TA (TCTA)$_3$ TCA (TCTA)$_2$ TCCATA (TCTA)$_9$ TCGTCT;

(SEQ ID NO: 24)
(TCTA)$_4$ (TCTG)$_6$ (TCTA)$_3$ TA (TCTA)$_3$ TCA (TCTA)$_2$ TCCATA (TCTA)$_{10}$ TCGTCT;

(SEQ ID NO: 25)
(TCTA)$_4$ (TCTG)$_6$ (TCTA)$_3$ TA (TCTA)$_3$ TCA (TCTA)$_2$ TCCATA (TCTA)$_{11}$ TCGTCT;

(SEQ ID NO: 26)
(TCTA)$_6$ (TCTG)$_5$ (TCTA)$_3$ TA (TCTA)$_3$ TCA (TCTA)$_2$ TCCATA (TCTA)$_{11}$ TCGTCT;

(SEQ ID NO: 27)
(TCTA)$_5$ (TCTG)$_6$ (TCTA)$_3$ TA (TCTA)$_3$ TCA (TCTA)$_2$ TCCATA (TCTA)$_{12}$ TCGTCT;

(SEQ ID NO: 28)
(TCTA)$_5$ (TCTG)$_6$ (TCTA)$_3$ TA (TCTA)$_3$ TCA (TCTA)$_2$ TCCATA (TCTA)$_{11}$ TA TCTA TCGTCT;

(SEQ ID NO: 29)
(TCTA)$_5$ (TCTG)$_6$ (TCTA)$_3$ TA (TCTA)$_3$ TCA (TCTA)$_2$ TCCATA (TCTA)$_{12}$ TA TCTA TCGTCT;

(SEQ ID NO: 30)
(TCTA)$_5$ (TCTG)$_6$ (TCTA)$_3$ TA (TCTA)$_3$ TCA (TCTA)$_2$ TCCATA (TCTA)$_{13}$ TA TCTA TCGTCT;

(SEQ ID NO: 31)
(TCTA)$_5$ (TCTG)$_6$ (TCTA)$_3$ TA (TCTA)$_3$ TCA (TCTA)$_2$ TCCATA (TCTA)$_{14}$ TATCTA TCGTCT;

(SEQ ID NO: 32)
(TCTA)$_{10}$ (TCTG)$_5$ (TCTA)$_3$ TA (TCTA)$_3$ TCA (TCTA)$_2$ TCCATA (TCTA)$_{12}$ TCGTCT;

(SEQ ID NO: 33)
(TCTA)$_{11}$ (TCTG)$_5$ (TCTA)$_3$ TA (TCTA)$_3$ TCA (TCTA)$_2$ TCCATA (TCTA)$_{12}$ TCGTCT;

(SEQ ID NO: 34)
(TCTA)$_{11}$ (TCTG)$_5$ (TCTA)$_3$ TA (TCTA)$_3$ TCA (TCTA)$_2$ TCCATA (TCTA)$_{13}$ TCGTCT;

(SEQ ID NO: 35)
(TCTA)$_{13}$ (TCTG)$_5$ (TCTA)$_3$ TA (TCTA)$_3$ TCA (TCTA)$_2$ TCCATA (TCTA)$_{12}$ TCGTCT; or (SEQ ID NO: 36)
(AGAA)$_8$;

Preferably the alleles are provided purified from alleles other than those of HUMVWFA31/A, HUMTHO1, D8S1179, HUMFIBRA/FGA, D21S11, D18S51 or AMG loci.

According to a fifth aspect of the invention we provide the use of an allelic ladder according to the first aspect of the invention and/or an allele according to the fourth aspect of the invention for comparison with a DNA analysis result.

The analysis may be a DNA profile of a sample. The profile may be based on analysis of one or more loci, in particular including one or more of HUMVWFA31/A, HUMTHO1, D8S1179, HUMFIBRA/FGA, D21S11, D18S51 or AMG. The sample may be from the scene of a crime, associated with the scene of a crime or comprise a bodily fluid sample. The sample may be used to compare two or more individuals, or samples arising therefrom, for instance in paternity and/or maternity analysis.

According to a sixth aspect of the invention we provide a method of producing an allelic ladder or mixture thereof by subjecting the ladders of the first, second or fourth aspects of the invention to PCR.

BRIEF DESCRIPTION OF THE DRAWINGS

The invention will now be described, by way of example only, and with reference to the accompanying figure in which:

FIGS. 1a and 1b illustrates the locus, allele designation and size for an embodiment of the invention;

FIG. 2f shows an electrophoretogram of the allelic ladder for D21S11;

FIG. 2g shows an electrophoretogram of the allelic ladder for D18S51;

FIG. 3a shows the sequence of selected alleles forming the HUMVWFA31/A ladder (SEQ ID NOS 1-2 and 39, respectively, in order of appearance);

FIG. 3b shows the sequence of selected alleles forming the HUMTHO1 ladder (SEQ ID NO: 4);

FIG. 3c shows the sequence of selected alleles forming the D8S1179 ladder (SEQ ID NOS 5-6, respectively, in order of appearance);

FIG. 3d shows the sequence of selected alleles forming the HUMFIBRA ladder (SEQ ID NOS 7-18, respectively, in order of appearance);

FIG. 3e shows the sequence of selected alleles forming the D21S11 ladder (SEQ ID NOS 19-35, respectively, in appearance); and FIG. 3f shows the sequence of selected alleles forming the D18S51 ladder (SEQ ID NO: 36).

DETAILED DESCRIPTION OF THE PREFERRED EMBODIMENTS

An allelic ladder mixture illustrative of the present invention is provided for loci HUMTHO1, D21S11, D8S1179, HUMVWFA31/A, HUMFIBRA/FGA and amelogenin sex test. The loci nomenclature is standard, corresponding to that used in the GENEBANK database.

The ladder mixture includes a significant number of alleles for each locus so as to provide a base line for comparison across a wide range. The loci, allelic designation and base pair sizes for the mixture are shown in FIGS. 1a and 1b. The nomenclature for the loci is discussed in Gill et al. 1996 *Int. Journal Leg. Med.* 109 14-22.

The allelic ladder mixture was presented in PARR buffer (containing Tris and 1.5 mM Mg ions at pH8.0) obtained from Cambio, primers obtained from Oswell and Taq polymerase from Perkin Elmer.

Figure 2A:
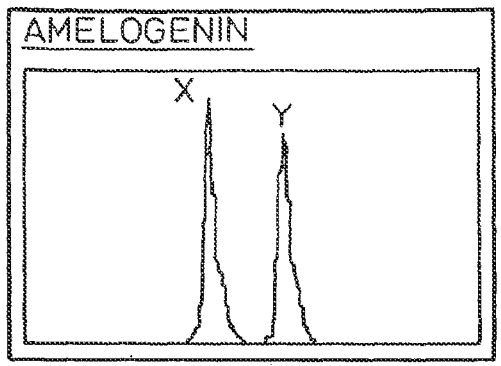
FIG. 2a shows an electrophoretogram of the allelic ladder for Amelogenin (AMG)
Figure 2B:
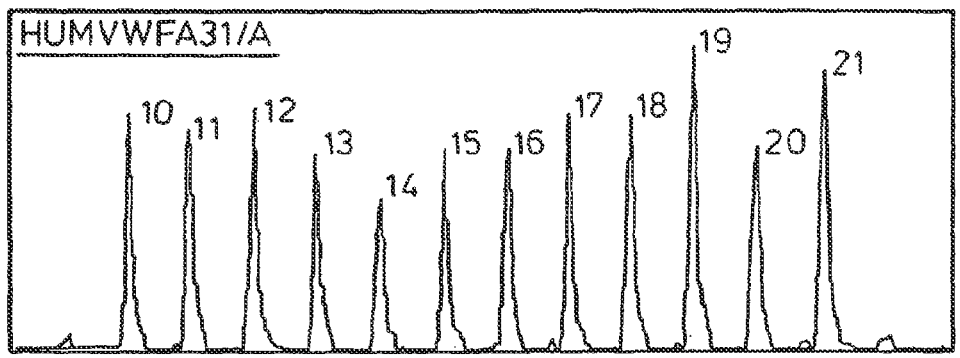
FIG. 2b shows an electrophoretogram of the allelic ladder for HUMVWFA31/A.
Figure 2C:
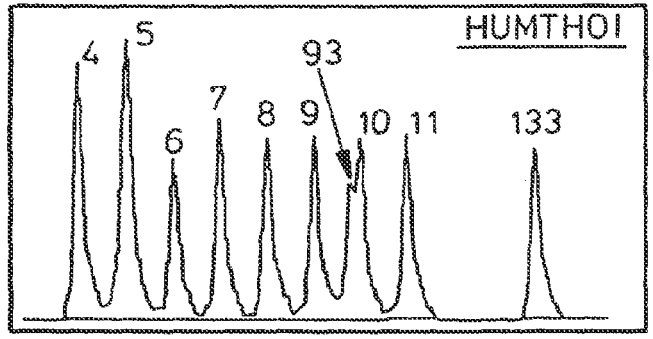
FIG. 2c shows an electrophoretogram of the allelic ladder for HUMTHO1.
Figure 2D:
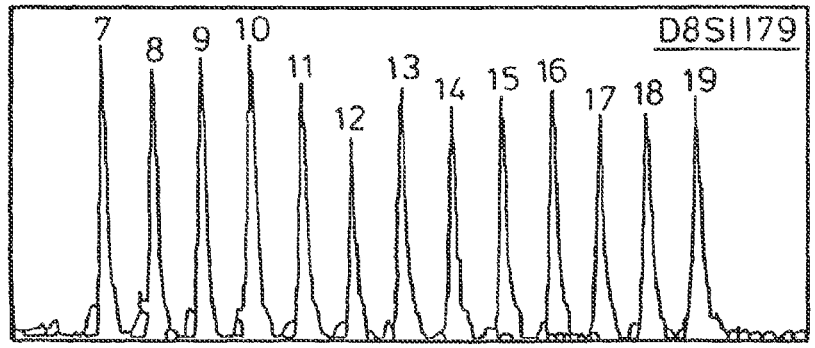
FIG. 2d shows an electrophoretogram of the allelic ladder for D8S1179.
Figure 2E:
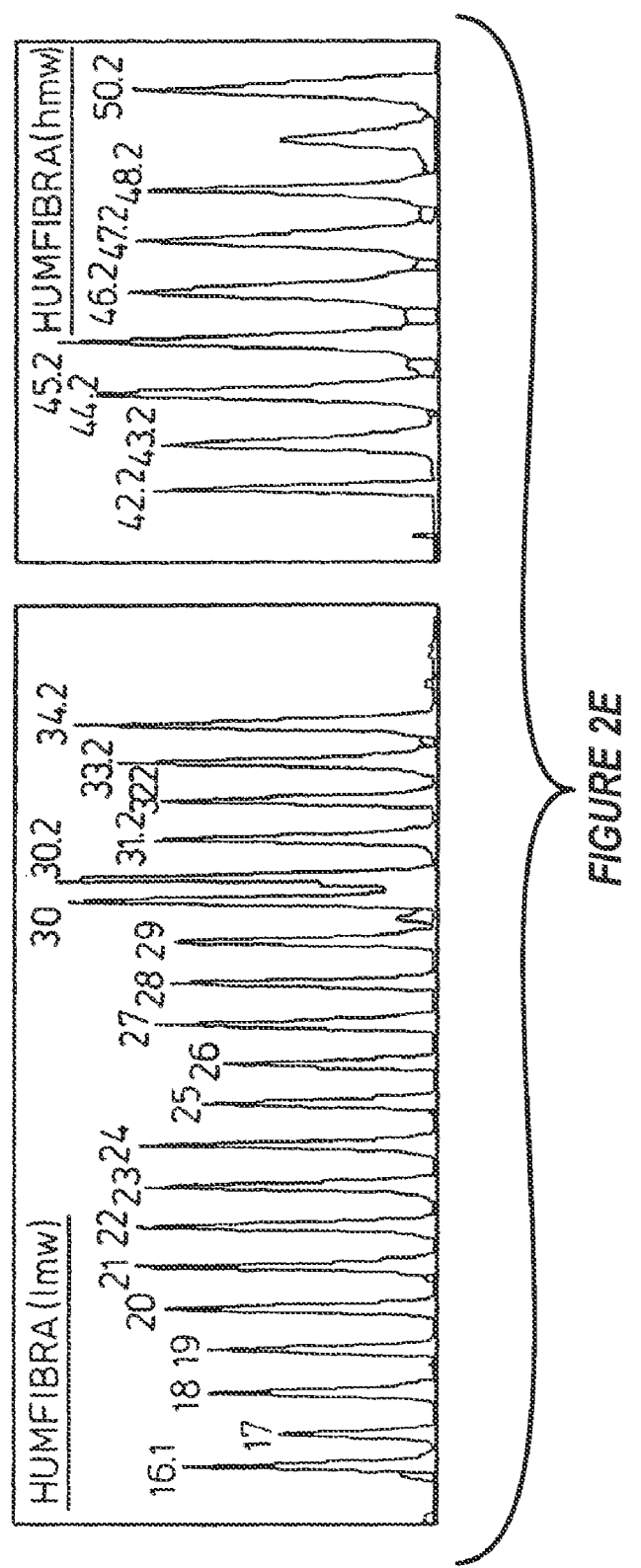
FIG. 2e shows an electrophoretogram of the allelic ladder for HUMFIBRA, low and high molecular weights.

Electrophoretograms for the allelic ladders are shown in FIGS. 2a to 2g with the allelic number designations shown.

FIGS. 3a to 3f show the sequences for the alleles identified in FIGS. 2a to 2g.

The allelic ladder mixture discussed above was produced according to the following techniques. Buccal swabs and/or bloodstains were used as the sample sources. The genomic DNA was extracted using the chelex procedure described by Walsh et al. 1991 *Bio. Techniques* 1 91-98.

The recovered DNA was quantified by dot hybridisation using a higher primate specific probe, as disclosed in Walsh et al. 1992 *Nucleic Acids Res.* 20 5061-5065.

Each sample was then amplified according to the conditions set out below in Table 1 with unlabelled oligonucleotide primers, the sequences for which are disclosed in Urquhart et al. 1995 *Bio Techniques* 18 116-121 and Oldroyd et al. 1995 *Electrophoresis* 16 334-337.

TABLE 1

| D18 | 95° C. for 60 seconds | D21 | 94° C. for 30 seconds |
|---|---|---|---|
|  | 60° C. for 60 seconds |  | 58° C. for 60 seconds |
|  | 72° C. for 60 seconds |  | 72° C. for 30 seconds |
| Method: 28 cycles + 72° C. | | Method: 26 cycles + 72° C. | |
| for 10 minutes | | for 10 minutes | |
| then hold at 4° C. | | then hold at 4° C. | |
| D8 | 94° C. for 30 seconds | TH01 | 94° C. for 45 seconds |
|  | 60° C. for 60 seconds | and | 60° C. for 60 seconds |
|  | 72° C. for 60 seconds | VWA | 72° C. for 60 seconds |
| Method: 30 cycles + 72° C. | | Method: 28 cycles + 72° C. | |
| for 10 minutes | | for 10 minutes | |
| then hold at 4° C. | | then hold at 4° C. | |
| FGA | 93° C. for 60 seconds | Amelo | 93° C. for 30 seconds |
|  | 60° C. for 60 seconds |  | 58° C. for 75 seconds |
|  | 72° C. for 60 seconds |  | 72° C. for 15 seconds |
| Method: 30 cycles + 72° C. | | Method: 30 cycles + 72° C. | |
| for 10 minutes | | for 10 minutes | |
| then hold at 4° C. | | then hold at 4° C. | |

Individual alleles were then isolated and sequence analysis was carried out according to the methods of Barber et al. 1996 *Int. Journal Leg. Med.* 108 180-185 and Barber and Parkin 1996 *Int. Journal Leg. Med.* 109 62-65. Both DNA strands of each allele reported were sequenced and the sequences provided in FIGS. 3a to 3g are the consensus results for this.

The illustrations of the alleles provided in FIGS. 3a to 3g follow the nomenclature recommended by the DNA commission of the International Society of Forensic Haemogenetics 1994 *Int. Journal Leg. Med.* 107 159-160 where the complete number of tandem repeats observed are designated by the digit. The longhand version of these sequences is provided at the end of the specific description.

To prepare the ladder cocktail amplification of the alleles is necessary. This process was performed by amplifying the purified single alleles described above using a labelled primer in each case. For the locus HUMFIBRA/FGA the ladder was produced from two separate mixes, discussed in more detail below. The primers used are disclosed in Urquhart et al. 1995 *Bio Techniques* 18 116-121 and Oldroyd et al. 1995 *Electrophoresis* 16 334-337 and were employed according to the conditions set out above in Table 1.

The singleplexs produced in this way were analysed on an Applied Biosystems 377 automated sequencer to confirm the sequences. The sequences obtained from the profiling system are one base longer than those determined form the DNA sequencing technique initially discussed above. This is due to the ability of DNA polymerase from *Thermus aquaticus* to catalyse a non-template mediated addition of a deoxyribonucleotide to the 3' hydroxyl of PCR products. This is generally known as the "n+1" product and can be generated in preference to the "n" product. The results reported here, however, refer to the "n" product rather than the "n+1" product for which the labelled primer PCR conditions have been optimised to produce.

The products of the amplification process for each locus were then diluted, mixed with one another and reanalysed to produce a single ladder for each loci having even peak heights. An initial level of 1000 Arbitary Units, AU, was increased to 1000-5000AU to give greater signal strength and volume for the ladder.

The single ladders produced in this way were then mixed together to give the cocktail discussed above. The proportions of each ladder used are controlled to give balanced peak areas. The cocktail was then validated using Applied Biosystems 373A and Applied Biosystems 377 automated sequencers with Genescan and Genotyper software.

Allelic ladders according to the invention can be prepared by applying PCR amplification techniques to a pre-existing sample of the allelic ladder mixture. Alternatively the allelic ladders can be constructed from the sequence information provided herein.

The new ladders disclosed above significantly extends the range of alleles which can be identified in any DNA profiling system.

The allelic ladder mixture is used as a control sample alongside samples from known or unknown individuals which are then segregated according to size in a gel. Alleles in the sample under test can be designated by the known alleles in the control if they are within 0.5 bases of one another. Alleles falling outside this range are estimated based on their position relative to the ladder.

Using the standard nomenclature discussed above, the ladder range for each locus, defined by the extreme low molecular weight and extreme high molecular weight alleles are:

| Locus | Low MW allele | High MW allele |
|---|---|---|
| HUMVWFA31/A | 10 | 21 |
| HUMTH01 | 4 | 13.3 |
| D8S1179 | 7 | 19 |
| HUMFIBRA/FGA | 16.1 | 50.2 |
| D21S11 | 53 | 81 |
| D18S51 | 8 | 27 |

The allelic ladders also enable the identification of certain rare and hence highly discriminatory alleles in DNA profiling, thus increasing the profiling systems power.

For the various locus certain alleles are of particular significance as follows:

Locus HUMTH01

The primers used for this locus were labelled with 6-FAM. The polymorphic region of this locus is based around a tetranucleotide motif repeat, $(TCAT)_n$, where n=4 to 13. Particular alleles provided by the present invention include 4, 9.3, 10 and 13.3. The 9.3 and 13.3 alleles were found to have a deletion of a thiamine nucleotide at either the last base of the 4th repeat unit or the first base of the 5th repeat unit. The 13.3 allele notably possesses a non-consensus tetranucleotide (TCGT) at the 13th repeat.

Locus D21S11

The primers for this locus were also labelled with 6-FAM. The allele range extends from 53 to 81 and significantly includes alleles 53, 56, 57, 79 and 81. The polymorphic region of the D21S11 alleles is relatively complex in structure and is based around the tetranucleotide TCTR, where R is A or G (following the ambiguity codes of the Nomenclature Committee of the International Union of Biochemistry), as well as containing invariant hexa-, tri- and di-nucleotides. Both allele 54 and allele 56 deviate from this general structure in that they possess a deletion of a 14 base pair $TA(TCTA)_3$ (SEQ ID NO: 37) unit immediately prior to the invariant TCA tetranucleotide.

Locus D18S51

Again primers with a 6-FAM label were used. The ladder extends to 20 distinct alleles with particularly significant alleles at 8, 9, 23, 24, 25, 26 and 27. The polymorphic region is based around a simple tetranucleotide repeat motif $(AGAA)_n$ (SEQ ID NO: 38), where n is 8 to 27.

Locus D8S1179

The primers used for this locus were labelled with TET. The ladder extends from alleles 7 to 19, based on 13 separate alleles. Significant alleles include 7, 15, 18 and 19. Different generalised structures were observed between the upper and lower molecular weight ends of the ladder. In the lower molecular weight area, 161 to 177 base pairs, a simple repeat region based on the tetranucleotide TCTA exists. In the higher weight region, 181 to 201 base pairs, a compound repeat region composed of the tetranucleotide TCTR was found.

Locus HUMVWFA31/A

HEX labelled primers were used for this locus. The ladder covers alleles between 10 and 21, based on 12 alleles in total. Noteworthy alleles 10, 11 and 12 are included. The polymorphic unit is generally composed of a compound repeat following the pattern $(TCTR)_n$. For the 13 and 14 alleles a non-consensus TCCA tetranucleotide at the 10th and 11th repeats was found.

Locus HUMFIBRA/FGA

This locus also employed HEX labelled primers. As mentioned above this ladder was constructed in two separate components. A low molecular weight and high molecular weight mix was used to produce the overall ladder. The low molecular weight mix ranges from allele 16.1 to 34.2 and the high molecular weight mix from allele 42.2 to 50.2.

The low MW mix includes significant alleles 16.1, 28, 30, 30.2, 31.2, 32.2, 33.2 and 34.2. The high MW mix includes noteworthy alleles 42.2, 43.2, 44.2, 45.2, 47.2, 48.2 and 50.2.

In general the HUMFIBRA/FGA alleles have a polymorphic unit based around the compound repeat YYBY, with the alleles in the upper part of the weight range being more complex in structure than those in the lower part. Within the general framework, allele 16.1 has a T nucleotide addition in the repeat region and allele 27 has a C to T transition in the 19th repeat unit (CTTT to CCTT). The upper MW allele range includes a stutter peak which is 4 base pairs smaller than the 50.2 allele. This artifact corresponds to allele 49.2 which has not currently been determined.

Amelogenin

Primers for this locus were once again labelled with 6-FAM. The sequence data revealed an X specific product of 105 base pairs and a Y specific product of 111 base pairs.

```
       HUMTH01 allele sequences
13.3 (TCAT)₄ CAT (TCAT)₇ TCGT TCAT                                              (SEQ ID NO: 4)

D21S11 alleles sequences
53   (TCTA)₄ (TCTG)₆ (TCTA)₃ TA(TCTA)₃ TCA (TCTA)₂ TCCATA (TCTA)₆ TCGTCT        (SEQ ID NO: 19)
```

-continued

| | | |
|---|---|---|
| 54 | (TCTA)₅ (TCTG)₆ (TCTA)₃ TCA (TCTA)₂ TCCATA (TCTA)₉ TCGTCT | (SEQ ID NO: 20) |
| 56 | (TCTA)₅ (TCTG)₆ (TCTA)₃ TCA (TCTA)₂ TCCATA (TCTA)₁₀ TCGTCT | (SEQ ID NO: 21) |
| 57 | (TCTA)₄ (TCTG)₆ (TCTA)₃ TA (TCTA)₃ TCA (TCTA)₂ TCCATA (TCTA)₈ TCGTCT | (SEQ ID NO: 22) |
| 59 | (TCTA)₅ (TCTG)₅ (TCTA)₃ TA (TCTA)₃ TCA (TCTA)₂ TCCATA (TCTA)₉ TCGTCT | (SEQ ID NO: 23) |
| 61 | (TCTA)₄ (TCTG)₆ (TCTA)₃ TA (TCTA)₃ TCA (TCTA)₂ TCCATA (TCTA)₁₀ TCGTCT | (SEQ ID NO: 24) |
| 63 | (TCTA)₄ (TCTG)₆ (TCTA)₃ TA (TCTA)₃ TCA (TCTA)₂ TCCATA (TCTA)₁₁ TCGTCT | (SEQ ID NO: 25) |
| 65 | (TCTA)₆ (TCTG)₅ (TCTA)₃ TA (TCTA)₃ TCA (TCTA)₂ TCCATA (TCTA)₁₁ TCGTCT | (SEQ ID NO: 26) |
| 67 | (TCTA)₅ (TCTG)₆ (TCTA)₃ TA (TCTA)₃ TCA (TCTA)₂ TCCATA (TCTA)₁₂ TCGTCT | (SEQ ID NO: 27) |
| 68 | (TCTA)₅ (TCTG)₆ (TCTA)₃ TA (TCTA)₃ TCA (TCTA)₂ TCCATA (TCTA)₁₁ TA TCTA TCGTCT | (SEQ ID NO: 28) |
| 70 | (TCTA)₅ (TCTG)₆ (TCTA)₃ TA (TCTA)₃ TCA (TCTA)₂ TCCATA (TCTA)₁₂ TA TCTA TCGTCT | (SEQ ID NO: 29) |
| 72 | (TCTA)₅ (TCTG)₆ (TCTA)₃ TA (TCTA)₃ TCA (TCTA)₂ TCCATA (TCTA)₁₃ TA TCTA TCGTCT | (SEQ ID NO: 30) |
| 74 | (TCTA)₅ (TCTG)₆ (TCTA)₃ TA (TCTA)₃ TCA (TCTA)₂ TCCATA (TCTA)₁₄ TATCTA TCGTCT | (SEQ ID NO: 31) |
| 75 | (TCTA)₁₀ (TCTG)₅ (TCTA)₃ TA (TCTA)₃ TCA (TCTA)₂ TCCATA (TCTA)₁₂ TCGTCT | (SEQ ID NO: 32) |
| 77 | (TCTA)₁₁ (TCTG)₅ (TCTA)₃ TA (TCTA)₃ TCA (TCTA)₂ TCCATA (TCTA)₁₂ TCGTCT | (SEQ ID NO: 33) |
| 79 | (TCTA)₁₁ (TCTG)₅ (TCTA)₃ TA (TCTA)₃ TCA (TCTA)₂ TCCATA (TCTA)₁₃ TCGTCT | (SEQ ID NO: 34) |
| 81 | (TCTA)₁₃ (TCTG)₅ (TCTA)₃ TA (TCTA)₃ TCA (TCTA)₂ TCCATA (TCTA)₁₂ TCGTCT | (SEQ ID NO: 35) |

D18S51 allele sequences

| | | |
|---|---|---|
| 8 | (AGAA)₈ | (SEQ ID NO: 36) |

D8S1179 allele sequences

| | | |
|---|---|---|
| 7 | (TCTA)₈ | (SEQ ID NO: 5) |
| 19 | (TCTA)₂ TCTG (TCTA)₁₆ | (SEQ ID NO: 6) |

HUMVWAF31/A allele sequences

| | | |
|---|---|---|
| 10 | TCTA TCTG TCTA (TCTG)₄ (TCTA)₃ | (SEQ ID NO: 1) |
| 12 | TCTA (TCTG)₄ (TCTA)₇ | (SEQ ID NO: 2) |
| 13 | (TCTA)₂ (TCTG)₄ (TCTA)₃ TCCA (TCTA)₃ | (SEQ ID NO: 3) |

(Note also that the allele has an atypical 3' flanking sequence. The usual sequence is TCCA TCTA T. In this allele the sequence is (TCCA)₂T.

HUMFIBRA(FGA) allele sequences

| | | |
|---|---|---|
| 16.1 | (TTTC)₃ TTTT TTCT (CTTT)₅ T (CTTT)₃ CTCC (TTCC)₂ | (SEQ ID NO: 7) |
| 27 | (TTTC)₃ TTTT TTCT (CTTT)₁₃ CCTT (CTTT)₅ CTCC (TTCC)₂ | (SEQ ID NO: 8) |
| 30 | (TTTC)₃ TTTT TTCT (CTTT)₁₆ CCTT (CTTT)₅ CTCC (TTCC)₂ | (SEQ ID NO: 9) |
| 31.2 | (TTTC)₄ TTTT TT (CTTT)₁₅ (CTTC)₃ (CTTT)₃ CTCC (TTCC)₄ | (SEQ ID NO: 10) |
| 32.2 | (TTTC)₄ TTTT TT (CTTT)₁₆ (CTTC)₃ (CTTT)₃ CTCC (TTCC)₄ | (SEQ ID NO: 11) |
| 33.2 | (TTTC)₄ TTTT TT (CTTT)₁₇ (CTTC)₃ (CTTT)₃ CTCC (TTCC)₄ | (SEQ ID NO: 12) |
| 42.2 | (TTTC)₄ TTTT TT (CTTT)₈ (CTGT)₄ (CTTT)₁₃ (CTTC)₄ (CTTT)₃ CTCC (TTCC)₄ | (SEQ ID NO: 13) |
| 43.2 | (TTTC)₄ TTTT TT (CTTT)₈ (CTGT)₅ (CTTT)₁₃ (CTTC)₄ (CTTT)₃ CTCC (TTCC)₄ | (SEQ ID NO: 14) |
| 44.2 | (TTTC)₄ TTTT TT (CTTT)₁₁ (CTGT)₃ (CTTT)₁₄ (CTTC)₃ (CTTT)₃ CTCC (TTCC)₄ | (SEQ ID NO: 15) |
| 45.2 | (TTTC)₄ TTTT TT (CTTT)₁₀ (CTGT)₅ (CTTT)₁₃ (CTTC)₄ (CTTT)₃ CTCC (TTCC)₄ | (SEQ ID NO: 16) |
| 47.2 | (TTTC)₄ TTTT TT (CTTT)₁₂ (CTGT)₅ (CTTT)₁₄ (CTTC)₃ (CTTT)₃ CTCC (TTCC)₄ | (SEQ ID NO: 17) |
| 48.2 | (TTTC)₄ TTTT TT (CTTT)₁₄ (CTGT)₃ (CTTT)₁₄ (CTTC)₄ (CTTT)₃ CTCC (TTCC)₄ | (SEQ ID NO: 18) |

The present invention may be embodied in other specific forms without departing form its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An allelic ladder mixture comprising one or more allelic ladders including an allelic ladder for locus HUMFIBRA/FGA comprising one or more alleles, at least one of which is an allele with a short tandem repeat sequence consisting of:

$$(TTTC)_4 \; TTTT \; TT \; (CTTT)_{14} \; (CTGT)_3 \; (CTTT)_{14} \; (CTTC)_4 \; (CTTT)_3 \; CTCC \; (TTCC)_4. \quad \text{(SEQ ID NO 18)}$$

2. An allelic ladder mixture according to claim 1 in which the mixture includes allelic ladders for a plurality of loci selected from HUMVWFA31/A, HUMTHO1, D8S1179, HUMFIBRA/FGA, D21S11 and D18S51.

3. An allelic ladder mixture according to claim 1 the mixture including allelic ladders for at least four loci.

4. An allelic ladder mixture according to claim 1 in which the allelic ladders in the mixture each include at least 7 alleles.

5. An allelic ladder mixture according to claim 1 in which the ladders, if present in the mixture, are provided such that: a HUMVWFA31/A allelic ladder includes at least 9 alleles; a HUMTHO1 allelic ladder includes at least 7 alleles; a D8S1179 allelic ladder includes at least 9 alleles; the HUMFIBRA/FGA allelic ladder includes at least 18 alleles or is present as HUMFIBRA/FGA/LW and HUMFIBRA/FGA/HW with the HUMFIBRA/FGA/LW ladder including at least 16 alleles, the HUMFIBRA/FGA/HW ladder including at least 6 alleles; a D21S11 allelic ladder includes at least 14 alleles; and a D18S51 ladder includes at least 15 alleles.

6. An allelic ladder mixture according to claim 1 in which one or more of the allelic ladders in the mixture comprises at least 4 pairs of alleles 4 base pairs from each other.

7. An allelic ladder mixture according to claim 1 in which the ladders, if present in the mixture, are provided such that: a HUMVWFA31/A allelic ladder includes at least 7 pairs of alleles 4 base pairs from each other; a HUMTHO1 allelic ladder includes at least 5 pairs of alleles 4 base pairs from each other; a D8S1179 allelic ladder includes at least 8 pairs of alleles 4 base pairs from each other; the HUMFIBRA/FGA allelic ladder includes at least 17 pairs of alleles 4 base pairs from each other; a D21S 11 allelic ladder includes at least 3 pairs of alleles 4 base pairs from each other; and a D18S51 ladder includes at least 13 pairs of alleles 4 base pairs from each other.

8. An allelic ladder mixture according to claim 7 in which the D21S11 allelic ladder includes at least 8 pairs of alleles 8 base pairs from each other.

9. An allelic ladder mixture according to claim 1 in which the ladders, if present, are provided such that a HUMVWFA31/A ladder includes alleles ranging from 130 base pairs upwards and/or from 166 base pairs downwards; a HUMTHO1 ladder includes alleles ranging from 150 base pairs upwards and/or 189 base pairs downwards; a D8S1179 ladder includes alleles ranging from 157 base pairs upwards and/or 201 base pairs downwards; the HUMFIBRA/FGA ladder includes alleles ranging from 173 base pairs upwards and/or 298 base pairs downwards; a D21S11 ladder includes alleles ranging from 203 base pairs upwards and/or 255 base pairs downwards; and a D18S51 ladder includes alleles ranging from 270 base pairs upwards and/or 326 downwards.

10. An allelic ladder mixture comprising an allelic ladder for the following locus, with lowest and highest allele designation as follows:

| Locus | Lowest Designation | Highest Designation |
|---|---|---|
| HUMFIBRA/FGA | 16.1 | 50.2 |

11. An allelic ladder mixture according to claim 10 in which the loci ladders have both the upper and lower limits specified.

12. An allelic ladder mixture according to claim 10 in which the mixture includes allelic ladders for loci HUMVWFA31/A, HUMTHO1, D8S1179, HUMFIBRA/FGA, D21S11 and D18S51.

13. A method of analysing one or more samples comprising:
 a) obtaining genomic DNA from the sample;
 b) amplifying the DNA;
 c) obtaining an indication of one or more of the constituent parts of the sample; and comparing the indications with an allelic ladder mixture comprising one or more allelic ladders including an allelic ladder for locus HUMFIBRA/FGA comprising one or more alleles, at least one of which is an allele with a short tandem repeat sequence consisting of:

(SEQ ID NO 18)
$(TTTC)_4$ TTTT TT $(CTTT)_{14}$ $(CTGT)_3$ $(CTTT)_{14}$ $(CTTC)_4$ $(CTTT)_3$ CTCC $(TTCC)_4$.

14. A method according to claim 13 in which the DNA sample is one or more of a sample taken from the scene of a crime, a sample associated with the scene of a crime, a sample obtained from a suspect, a sample obtained from a human under consideration or a reference sample.

15. A method according to claim 13 in which the sample is amplified using a polymerase chain reaction and primers for one or more of loci HUMVWFA31/A, HUMTHO1, D8S1179, HUMFIBRA/FGA, D21S11 or D18S51 are employed.

16. A kit of parts including an allelic ladder mixture comprising one or more allelic ladders and including an allelic ladder for locus HUMFIBRA/FGA comprising an allele with a short tandem repeat sequence consisting of sequence:

(SEQ ID NO 18)
$(TTTC)_4$ TTTT TT $(CTTT)_{14}$ $(CTGT)_3$ $(CTTT)_{14}$ $(CTTC)_4$ $(CTTT)_3$ CTCC $(TTCC)_4$;

the kit of parts further include one or more of
 PARR buffer, one or more primers, or Taq polymerase.

17. An allelic ladder mixture comprising at least an allelic ladder for locus D21S11 comprising one or more alleles, at least one of which is an allele with a short tandem repeat sequence consisting of (SEQ ID NO: 32)
$(TCTA)_{10}$ $(TCTG)_5$ $(TCTA)_3$ TA $(TCTA)_3$ TCA $(TCTA)_2$ TCCATA $(TCTA)_{12}$ TCGTCT.

18. An allelic ladder mixture according to claim 17 in which the mixture includes allelic ladders for a plurality of loci selected from HUMVWFA31/A, HUMTHO1, D8S1179, HUMFIBRA/FGA, D21S11 and D18S51.

19. An allelic ladder mixture according to claim 17 the mixture including allelic ladders for at least four loci.

20. An allelic ladder mixture according to claim 17 in which the allelic ladders in the mixture includes at least 7 alleles.

21. An allelic ladder mixture according to claim 17 in which the ladders, if present in the mixture, are provided such that: a HUMVWFA31/A allelic ladder includes at least 9 alleles; a HUMTHO1 allelic ladder includes at least 7 alleles; a D8S1179 allelic ladder includes at least 9 alleles; a HUMFIBRA/FGA allelic ladder includes at least 18 alleles or is present as HUMFIBRA/FGA/LW and HUMFIBRA/FGA/HW with the HUMFIBRA/FGA/LW ladder including at least 16 alleles, the HUMFIBRA/FGA/HW ladder including at least 6 alleles; the D21S11 allelic ladder includes at least 14 alleles; and a D18S51 ladder includes at least 15 alleles.

22. An allelic ladder mixture according to claim 17 in which one or more of the allelic ladders in the mixture comprises at least 4 pairs of alleles 4 base pairs from each other.

23. An allelic ladder mixture according to claim 17 in which the ladders, if present in the mixture, are provided such that: a HUMVWFA31/A allelic ladder includes at least 7 pairs of alleles 4 base pairs from each other; a HUMTHO1 allelic ladder includes at least 5 pairs of alleles 4 base pairs from each other; a D8S1179 allelic ladder includes at least 8 pairs of alleles 4 base pairs from each other; a HUMFIBRA/FGA allelic ladder includes at least 17 pairs of alleles 4 base pairs from each other; the D21S 11 allelic ladder includes at least 3 pairs of alleles 4 base pairs from each other; and a D18S51 ladder includes at least 13 pairs of alleles 4 base pairs from each other.

24. An allelic ladder mixture according to claim 23 in which the D21S11 allelic ladder includes at least 8 pairs of alleles 8 base pairs from each other.

25. An allelic ladder mixture according to claim 17 in which the ladders, if present, are provided such that a HUMVWFA31/A ladder includes alleles ranging from 130 base pairs upwards and/or from 166 base pairs downwards; a HUMTHO1 ladder includes alleles ranging from 150 base pairs upwards and/or 189 base pairs downwards; a D8S1179 ladder includes alleles ranging from 157 base pairs upwards and/or 201 base pairs downwards; a HUMFIBRA/FGA ladder includes alleles ranging from 173 base pairs upwards and/or 298 base pairs downwards; the D21S 11 ladder includes alleles ranging from 203 base pairs upwards and/or 255 base pairs downwards; and a D18S51 ladder includes alleles ranging from 270 base pairs upwards and/or 326 downwards.

26. A method of analysing one or more samples comprising:
  a) obtaining genomic DNA from the sample;
  b) amplifying the DNA;
  c) obtaining an indication of one or more of the constituent parts of the sample; and comparing the indications with an allelic ladder mixture comprising one or more allelic ladders including an allelic ladder for locus D21S11 comprising one or more alleles, at least one of which is an allele with a short tandem repeat sequence consisting of:

(TCTA)$_{10}$ (TCTG)$_5$ (TCTA)$_3$ TA (TCTA)$_3$ TCA (TCTA)$_2$ (SEQ ID NO: 32)

TCCATA (TCTA)$_{12}$ TCGTCT.

27. A method according to claim 26 in which the DNA sample is one or more of a sample taken from the scene of a crime, a sample associated with the scene of a crime, a sample obtained from a suspect, a sample obtained from a human under consideration (for instance for paternity or maternity analysis) or a reference sample.

28. A method according to claim 26 in which the sample is amplified using a polymerase chain reaction and primers for one or more of loci HUMVWFA31/A, HUMTHO1, D8S1179, HUMFIBRA/FGA, D21S11 or D18S51 are employed.

29. A kit of parts including an allelic ladder mixture comprising one or more allelic ladders and including an allelic ladder for locus D21S 11 comprising an allele with a short tandem repeat sequence consisting of sequence:

(TCTA)$_{10}$ (TCTG)$_5$ (TCTA)$_3$ TA (TCTA)$_3$ TCA (TCTA)$_2$ (SEQ ID NO: 32)

TCCATA (TCTA)$_{12}$ TCGTCT;

the kit of parts further including one or more of:
    PARR buffer, one or more primers or Taq polymerase.

30. An allelic ladder mixture comprising one or more allelic ladders including an allelic ladder for locus D21S11 comprising one or more alleles, at least one of which is an allele with a short tandem repeat sequence consisting of:

(TCTA)$_{11}$ (TCTG)$_5$ (TCTA)$_3$ TA (TCTA)$_3$ TCA (TCTA)$_2$ (SEQ ID NO: 33)

TCCATA (TCTA)$_{12}$ TCGTCT.

31. An allelic ladder mixture according to claim 30 in which the mixture includes allelic ladders for a plurality of loci selected from HUMVWFA31/A, HUMTHO1, D8S1179, HUMFIBRA/FGA, D21S11 and D18S51.

32. An allelic ladder mixture according to claim 30 the mixture including allelic ladders for at least four loci.

33. An allelic ladder mixture according to claim 30 in which the allelic ladders in the mixture includes at least 7 alleles.

34. An allelic ladder mixture according to claim 30 in which the ladders, if present in the mixture, are provided such that: a HUMVWFA31/A allelic ladder includes at least 9 alleles; a HUMTHO1 allelic ladder includes at least 7 alleles; a D8S1179 allelic ladder includes at least 9 alleles; a HUMFIBRA/FGA allelic ladder includes at least 18 alleles or is present as HUMFIBRA/FGA/LW and HUMFIBRA/FGA/HW with the HUMFIBRA/FGA/LW ladder including at least 16 alleles, the HUMFIBRA/FGA/HW ladder including at least 6 alleles; the D21S11 allelic ladder includes at least 14 alleles; and a D18S51 ladder includes at least 15 alleles.

35. An allelic ladder mixture according to claim 30 in which one or more of the allelic ladders in the mixture comprises at least 4 pairs of alleles 4 base pairs from each other.

36. An allelic ladder mixture according to claim 30 in which the ladders, if present in the mixture, are provided such that: a HUMVWFA31/A allelic ladder includes at least 7 pairs of alleles 4 base pairs from each other; a HUMTHO1 allelic ladder includes at least 5 pairs of alleles 4 base pairs from each other; a D8S1179 allelic ladder includes at least 8 pairs of alleles 4 base pairs from each other; a HUMFIBRA/FGA allelic ladder includes at least 17 pairs of alleles 4 base pairs from each other; the D21S 11 allelic ladder includes at least 3 pairs of alleles 4 base pairs from each other; and a D18S51 ladder includes at least 13 pairs of alleles 4 base pairs from each other.

37. An allelic ladder mixture according to claim 36 in which the D21S11 allelic ladder includes at least 8 pairs of alleles 8 base pairs from each other.

38. An allelic ladder mixture according to claim 30 in which the ladders, if present, are provided such that a HUMVWFA31/A ladder includes alleles ranging from 130 base pairs upwards and/or from 166 base pairs downwards; a HUMTHO1 ladder includes alleles ranging from 150 base pairs upwards and/or 189 base pairs downwards; a D8S1179 ladder includes alleles ranging from 157 base pairs upwards and/or 201 base pairs downwards; a HUMFIBRA/FGA ladder includes alleles ranging from 173 base pairs upwards and/or 298 base pairs downwards; the D21S 11 ladder includes alleles ranging from 203 base pairs upwards and/or 255 base pairs downwards; and a D18S51 ladder includes alleles ranging from 270 base pairs upwards and/or 326 downwards.

39. An allelic ladder mixture comprising an allelic ladder for the following locus, with lowest and highest allele designations as follows:

| Locus | Lowest allele designation | Highest allele designation |
|---|---|---|
| D21S11 | 53 | 81. |

40. A method of analysing one or more samples comprising:
  a) obtaining genomic DNA from the sample;
  b) amplifying the DNA;
  c) obtaining an indication of one or more of the constituent parts of the sample; and comparing the indications with an allelic ladder mixture comprising one or more allelic ladders including an allelic ladder for locus D21S11 comprising one or more alleles, at least one of which is an allele with a short tandem repeat sequence consisting of:

(TCTA)$_{11}$ (TCTG)$_5$ (TCTA)$_3$ TA (TCTA)$_3$ TCA (TCTA)$_2$ (SEQ ID NO: 33)

TCCATA (TCTA)$_{12}$ TCGTCT.

41. A method according to claim 40 in which the DNA sample is one or more of a sample taken from the scene of a crime, a sample associated with the scene of a crime, a sample obtained from a suspect, a sample obtained from a human under consideration (for instance for paternity or maternity analysis) or a reference sample.

42. A method according to claim 40 in which the sample is amplified using a polymerase chain reaction and primers for one or more of loci HUMVWFA31/A, HUMTHO1, D8S1179, HUMFIBRA/FGA, D21S11 or D18S51 are employed.

43. A kit of parts including an allelic ladder mixture comprising one or more allelic ladders and including an allelic ladder for locus D21S 11 comprising an allele with a short tandem repeat sequence consisting of sequence:

(SEQ ID NO: 33)
(TCTA)$_{11}$ (TCTG)$_5$ (TCTA)$_3$ TA (TCTA)$_3$ TCA (TCTA)$_2$
TCCATA (TCTA)$_{12}$ TCGTCT;

the kit of parts further include one or more of
PARR buffer, one or more primers, or Taq polymerase.

44. An allelic ladder mixture comprising one or more allelic ladders including an allelic ladder for locus D21S11 comprising one or more alleles, at least one of which is an allele with a short tandem repeat sequence consisting of:

(SEQ ID NO: 34)
(TCTA)$_{11}$ (TCTG)$_5$ (TCTA)$_3$ TA (TCTA)$_3$ TCA (TCTA)$_2$
TCCATA (TCTA)$_{13}$ TCGTCT.

45. An allelic ladder mixture according to claim 44 in which the mixture includes allelic ladders for a plurality of loci selected from hUMVWFA31/A, HUMTHO1, D8S1179, HUMFIBRA/FGA, D21S11 and D18S51.

46. An allelic ladder mixture according to claim 44 the mixture including allelic ladders for at least four loci.

47. An allelic ladder mixture according to claim 44 in which the allelic ladders in the mixture includes at least 7 alleles.

48. An allelic ladder mixture according to claim 44 in which the ladders, if present in the mixture, are provided such that: a HUMVWFA31/A allelic ladder includes at least 9 alleles; a HUMITHO1 allelic ladder includes at least 7 alleles; a D8S1179 allelic ladder includes at least 9 alleles; a HUMFIBRA/FGA allelic ladder includes at least 18 alleles or is present as HUMFIBRA/FGA/LW and HUMFIBRA/FGA/HW with the HUMFIBRA/FGA/LW ladder including at least 16 alleles, a HUMFIBRA/FGA/HW ladder including at least 6 alleles; the D21S11 allelic ladder includes at least 14 alleles; and a D18S51 ladder includes at least 15 alleles.

49. An allelic ladder mixture according to claim 44 in which one or more of the allelic ladders in the mixture comprises at least 4 pairs of alleles 4 base pairs from each other.

50. An allelic ladder mixture according to claim 44 in which the ladders, if present in the mixture, are provided such that: a HUMVWFA31/A allelic ladder includes at least 7 pairs of alleles 4 base pairs from each other; a HUMTHO1 allelic ladder includes at least 5 pairs of alleles 4 base pairs from each other; a D8S1179 allelic ladder includes at least 8 pairs of alleles 4 base pairs from each other; a HUMFIBRA/FGA allelic ladder includes at least 17 pairs of alleles 4 base pairs from each other; the D21S 11 allelic ladder includes at least 3 pairs of alleles 4 base pairs from each other; and a D18S51 ladder includes at least 13 pairs of alleles 4 base pairs from each other.

51. An allelic ladder mixture according to claim 50 in which the D21S11 allelic ladder includes at least 8 pairs of alleles 8 base pairs from each other.

52. An allelic ladder mixture according to claim 44 in which the ladders, if present, are provided such that a HUMVWFA31/A ladder includes alleles ranging from 130 base pairs upwards and/or from 166 base pairs downwards; a HUMTHO1 ladder includes alleles ranging from 150 base pairs upwards and/or 189 base pairs downwards; a D8S1179 ladder includes alleles ranging from 157 base pairs upwards and/or 201 base pairs downwards; a HUMFIBRA/FGA ladder includes alleles ranging from 173 base pairs upwards and/or 298 base pairs downwards; the D21S 11 ladder includes alleles ranging from 203 base pairs upwards and/or 255 base pairs downwards; and a D18S51 ladder includes alleles ranging from 270 base pairs upwards and/or 326 downwards.

53. A method of analysing one or more samples comprising:
a) obtaining genomic DNA from the sample;
b) amplifying the DNA;
c) obtaining an indication of one or more of the constituent parts of the sample; and comparing the indications with an allelic ladder mixture comprising one or more allelic ladders including an allelic ladder for locus D21S11 comprising one or more alleles, at least one of which is an allele with a short tandem repeat sequence consisting of:

(SEQ ID NO: 34)
(TCTA)$_{11}$ (TCTG)$_5$ (TCTA)$_3$ TA (TCTA)$_3$ TCA (TCTA)$_2$
TCCATA (TCTA)$_{13}$ TCGTCT.

54. A method according to claim 53 in which the DNA sample is one or more of a sample taken from the scene of a crime, a sample associated with the scene of a crime, a sample obtained from a suspect, a sample obtained from a human under consideration or a reference sample.

55. A method according to claim 53 in which the sample is amplified using a polymerase chain reaction and primers for one or more of loci HUMVWFA31/A, HUMTHO1, D8S1179, HUMFIBRA/FGA, D21S11 or D18S51 are employed.

56. A kit of parts including an allelic ladder mixture comprising one or more allelic ladders and including an allelic ladder for locus D21S11 comprising an allele with a short tandem repeat sequence consisting of sequence:

(SEQ ID NO: 34)
(TCTA)$_{11}$ (TCTG)$_5$ (TCTA)$_3$ TA (TCTA)$_3$ TCA (TCTA)$_2$
TCCATA (TCTA)$_{13}$ TCGTCT;

the kit of parts further include one or more of
PARR buffer, one or more primers or Taq polymerase.

* * * * *